US007842709B2

(12) United States Patent
Tartaglia et al.

(10) Patent No.: US 7,842,709 B2
(45) Date of Patent: Nov. 30, 2010

(54) METHOD FOR TREATING INFLAMMATORY DISEASES OF THE DIGESTIVE TRACT

(75) Inventors: Louis Anthony Tartaglia, Newton, MA (US); Thomas Michael Barnes, Brookline, MA (US); Robert Mark Coopersmith, Chestnut Hill, MA (US); Scott Edward Malstrom, Reading, MA (US); David William White, Norwell, MA (US); Dominic Picarella, Sudbury, MA (US)

(73) Assignee: Ore Pharmaceuticals Inc., Cambridge, MA (US)

( * ) Notice: Subject to any disclaimer, the term of this patent is extended or adjusted under 35 U.S.C. 154(b) by 234 days.

(21) Appl. No.: 11/851,669

(22) Filed: Sep. 7, 2007

(65) Prior Publication Data

US 2008/0107650 A1 May 8, 2008

Related U.S. Application Data

(60) Provisional application No. 60/825,058, filed on Sep. 8, 2006, provisional application No. 60/827,795, filed on Oct. 2, 2006.

(51) Int. Cl.
    *A61K 31/417* (2006.01)

(52) U.S. Cl. .................................... 514/400

(58) Field of Classification Search ........................ None
    See application file for complete search history.

(56) References Cited

U.S. PATENT DOCUMENTS

| 6,194,556 | B1 | 2/2001 | Acton et al. ............... 536/23.2 |
| 6,632,830 | B1 | 10/2003 | Acton et al. ............... 514/365 |
| 6,900,033 | B2 | 5/2005 | Parry et al. ................ 435/69.1 |
| 7,045,532 | B2 * | 5/2006 | Acton et al. ................ 514/311 |
| 2004/0082496 | A1 | 4/2004 | Acton et al. ................... 514/1 |
| 2005/0203168 | A1 | 9/2005 | Teitelbaum et al. ......... 514/423 |

OTHER PUBLICATIONS

The Merck Manual, 17th edition (1999), pp. 302-307.*
Riaz et al., FASEB J., (May, 2004), 18(7), pp. 881-3 (Abstract).*
Best et al. (1976) *Gastroenterology* 70(3), 439-444.
Bonner (2003) "Inflammatory bowel disease: advances in medical management." http://www.fascrs.org/displaycommon.cfm?an=1&subarticlenbr=113.
Burrel et al. (2005) *Eur. Heart. J.* 26, 369-375.
Byrne et al. (2006) *Current Opin. In Drug Discovery & Develop.* 8(2), 207-217.
Carlsen et al. (2002) *J. Immunool.* 168, 1441-1446.
Costanzo et al. (2003) *J. Cell. Physiol.* 195(3),402-410.
Crackower et al. (2002) *Nature* 417(6891), 822-828.
Dales et al. (2002) *J. Am. Chem. Soc.* 124(40), 11852-11853.
Donoghue et al. (2000) *Circ. Res.* 87, 1-9.
Esteban et al. (2004) *J. Am. Soc. Nephrol.* 15, 1514-1529.
Ferreira & Santos (2005) *Braz. J. Med. Biol. Res.* 38, 499-507.
Fichtner-Feigl et al. (2005) J. Clin. Invest. 115(11), 3057-3071.
Gembardt et al. (2005) *Peptides* 26, 1270-1277.
Guidi et al. (2005) *Int. J. Immunopathol. Pharmacol.* 18(1), 155-164.
Guy et al. (2005) *Biochim. Biophys. Acta* 1751(1), 2-8.
Harmer et al. (2002) *FEBS Lett.* 532, 107-110.
Hollenbach et al. (2004) *FASEB J.* 18(13), 1550-1552.
Huang et al. (2003) *J. Biol. Chem.* 278(18), 15532-15540.
Huentelman et al. (2004) *Hypertension* 44, 903-906.
Huentelman et al. (2005) *Exp. Physiol.* 90(5), 783-790.
Imai et al. (2005) *Nature* 436(7047), 112-116.
Inokuchi et al. (2005) *Gut* 54, 349-356.
Jersmann et al. (2001) *Infection and Immunity* 69(3), 1273-1279.
Komatsu et al. (2002) *DNA Seq.* 13(4), 217-220.
Li et al. (2005) *Am. J. Physiol. Renal Physiol.* 288, F353-F362.
Mendes et al. (2005) *Regul. Pent.* 125(1-3), 29-34.
Naber & de Jong (2003) *Neth. J. Med.* 61(4), 105-110.
Nikolaus et al. (2000) *Lancet* 356(9240), 1475-1479.
Phillips & Kagiyama (2002) *Curr. Opin. Investig. Drugs* 3(4), 569-577.
Rice et al. (2001) *J. Biomed. Opt.* 6(4), 432-440.
Rice et al. (2003) *Bull. Br. Soc. Cardiovasc. Res.* 16(2), 5-11.
Sanz-Rosa et al. (2005) *Am. J. Physiol. Heart Circ. Physiol.* 288, H111-H-115.
Schreiber et al. (1998) *Gut* 42, 477-484.
Tallant & Clark (2003) *Hypertension* 42, 574-579.
Tipnis et al. (2000) *J. Biol. Chem.* 275(43) 33238-33243.
Tung & Warner (2002) Postgraduate Medicine 112(5). "Colonic inflammatory bowel disease: medical therapies for colonic Crohn's disease and ulcerative colitis." http://www.postgradrmed.com/issues/2002/11_02/tung2.htm.
University of Maryland Medical Center (2002) "What are the Drug Treatments for Inflammatory Bowel Disease?" http://www.umm.edu/patiented/articles/what_drugtreatments_inflammatory_bowel_disease_0000693.9.htm.

* cited by examiner

*Primary Examiner*—Phyllis G. Spivack
(74) *Attorney, Agent, or Firm*—Harness, Dickey & Pierce, P.L.C.; J. Timothy Keane; Kisuk Lee

(57) ABSTRACT

A method for treating an inflammatory disease of the digestive tract, for example inflammatory bowel disease, in a subject comprises administering to the subject a therapeutically effective amount of a compound selected from the group consisting of (S,S)-2-[1-carboxy-2-[3-(3,5-dichlorobenzyl)-3H-imidazol-4-yl]-ethylamino]-4-methylpentanoic acid and pharmaceutically acceptable salts thereof.

19 Claims, 13 Drawing Sheets

DSS + vehicle

DSS + GL1001, 100 mg/kg/day

METHOD FOR TREATING INFLAMMATORY DISEASES OF THE DIGESTIVE TRACT

This application claims the benefit of U.S. provisional patent application Ser. No. 60/825,058, filed on Sep. 8, 2006, and Ser. No. 60/827,795, filed on Oct. 2, 2006, the entire disclosure of each of which is incorporated by reference herein.

FIELD OF THE INVENTION

The present invention relates to pharmacotherapy for inflammatory diseases of the digestive tract such as chronic gastritis and inflammatory bowel disease (IBD).

BACKGROUND

General Background of IBD

The digestive tract, also referred to as the alimentary canal (nourishment canal) or the gut, is part of the digestive system, i.e., the system of organs within multicellular animals which takes in food, digests it to extract energy and nutrients, and expels the remaining waste. This process is called digestion. As defined herein, the digestive tract includes those organs through which food or solid excreta pass in the course of the digestive process, but excludes those organs of the digestive system, adjacent to and connecting with the digestive tract, that store and/or secrete substances aiding in digestion, for example liver, gallbladder and pancreas. This definition is broadly consistent with that given in standard reference works such as *Dorland's Illustrated Medical Dictionary*, 30th ed. (2003), Saunders, Philadelphia, which defines the digestive tract as that part of the digestive system formed by the esophagus, stomach and intestines, except that for convenience herein the mouth and pharynx are also included. In a normal human adult male, the digestive tract from mouth to anus is approximately 7.5 meters long and consists of upper and lower portions with the following components:

upper digestive tract: mouth (oral or buccal cavity; includes salivary glands, oral mucosa, teeth and tongue), pharynx, esophagus (gullet) and cardia, stomach, which includes the antrum and pylorus and the pyloric sphincter;

lower digestive tract: bowel or intestines, consisting of (a) small intestine, which has three parts: duodenum, jejunum and ileum; (b) large intestine, which has three parts: cecum (including the vermiform appendix which is a diverticulum of the cecum), colon (ascending colon, transverse colon, descending colon and sigmoid flexure), and rectum; and (c) anus.

The term "gastrointestinal tract" or "GI tract" is sometimes used herein, as commonly in the art, to refer to the entire digestive tract. If used in its strict sense, meaning that part of the digestive tract formed by stomach and intestines, such use is expressly specified herein or will be required by the context.

Inflammatory bowel disease (IBD) is a class of idiopathic diseases of the digestive tract that are believed to involve an autoimmune reaction. Two major types of IBD are recognized: ulcerative colitis (UC) and Crohn's disease (CD). UC, also known as idiopathic proctocolitis, is typically limited to the colon; CD, also referred to as regional enteritis, terminal ileitis or granulomatous ileocolitis, can involve any segment or segments of the digestive tract from the mouth to the anus. Where the term "inflammatory bowel disease" or "IBD" is used herein, particularly with reference to CD, it will be understood to include manifestations anywhere in the digestive tract, not exclusively in the bowel.

UC and CD exhibit significant differences, but both diseases share a number of intestinal and extraintestinal manifestations, although some of these tend to occur more commonly in one disease or the other. Both UC and CD usually exhibit waxing and waning intensity and severity. When an IBD patient has symptoms indicating significant inflammation, the disease is considered to be in an active stage; such a patient is said to be having a "flare" of the IBD. When inflammation is of lesser severity or absent and the patient substantially asymptomatic, the disease is considered to be in remission. In most cases, symptoms correspond well with the degree of inflammation present for either disease, although this is not universally true. In some patients, objective evidence for disease activity may be needed before administering medications with potential for significant adverse side effects.

Information on IBD, its symptoms, pathology and treatment can be found in various print and internet sources, including for example those individually cited below and incorporated herein by reference.

Bonner (2003) "Inflammatory bowel disease: advances in medical management." http://www.fascrs.org/displaycommon.cfm?an=1&subarticlenbr=113.

Tung & Warner (2002) *Postgraduate Medicine* 112(5). "Colonic inflammatory bowel disease: medical therapies for colonic Crohn's disease and ulcerative colitis." http://www.postgradmed.com/issues/2002/11_02/tung2.htm.

University of Maryland Medical Center (2002) "What are the Drug Treatments for Inflammatory Bowel Disease?" http://www.umm.edu/patiented/articles/what_drug_treatments_inflammatory_bowel_disease_000069_9.htm.

Ulcerative Colitis: Symptoms and Pathology

Patients with UC most commonly present with bloody diarrhea. Abdominal pain and cramping, fever and weight loss occur in more severe cases. The greater the extent of colon involvement, the more likely the patient is to have diarrhea. Rectal urgency (tenesmus) can be associated with inflamed rectum. Patients might have formed stools if their disease is confined to the rectum. As the degree of inflammation increases, systemic symptoms develop, including low-grade fever, malaise, nausea, vomiting, sweats and arthralgias. Fever, dehydration and abdominal tenderness develop in severe UC, reflecting progressive inflammation into deeper layers of the colon.

Diagnosis of UC can be made endoscopically or radiologically, with contrast radiographs typically showing loss of the normal mucosal pattern and, with more advanced disease, loss of colonic haustrae. Sigmoidoscopy or colonoscopy reveals that the rectum is almost always involved. The disease can be limited to the rectum (proctitis), in about 25% of patients; to the rectum, sigmoid, and descending colon (left-sided colitis), in most patients; or to the entire colon (pancolitis), in about 10% of patients. UC does not involve any other segment of the gastrointestinal tract. Colectomy is curative.

In UC, a clear demarcation exists between involved and uninvolved mucosa; and in the involved area, the disease is strikingly and uniformly continuous. UC primarily involves the mucosa and the submucosa, with formation of crypt abscesses and mucosal ulceration. The mucosa typically appears granular and friable. In more severe cases, pseudopolyps form, consisting of areas of hyperplastic growth with swollen mucosa surrounded by inflamed mucosa with shallow ulcers. In severe UC, inflammation and necrosis can extend below the lamina propria to involve the submucosa and the circular and longitudinal muscles, although this is unusual. As the disease becomes chronic, the colon becomes a rigid foreshortened tube that lacks its usual haustral (out-pouch) markings, leading to the "lead pipe" appearance observed on barium enema.

Regarding prognosis for UC, only a small percentage of patients have a single attack and no recurrence. Typically, however, remissions and exacerbations are characteristic of UC, with acute attacks lasting weeks to months. Twenty percent of patients require colectomy, which is curative. Long-term morbidity primarily results from complications of medical therapy, especially long-term steroids.

The most common causes of death in IBD are peritonitis with sepsis, malignancy, thromboembolic disease, and complications of surgery. Toxic megacolon, one of the most dreaded complications of UC, can lead to perforation, sepsis, and death. Malignancy is the most dreaded long-term intestinal complication of UC, as the risk of colon cancer begins to rise significantly above that of the general population approximately 8-10 years after diagnosis. Colonic strictures in persons with UC are presumed to be malignant unless proven otherwise (usually by resection).

Crohn's Disease: Symptoms and Pathology

The presentation of CD is generally more insidious than that of UC, with ongoing abdominal pain, anorexia, diarrhea, weight loss and fatigue. Grossly bloody stools, while typical of UC, are less common in CD. Stools may be formed, but loose stools predominate if the colon or the terminal ileum is involved extensively. One half of patients with CD present with perianal disease (e.g., fistulas or abscesses). Occasionally, acute right lower quadrant pain and fever may be noted, mimicking appendicitis. Commonly, the diagnosis is established only after several years of recurrent abdominal pain, fever, and diarrhea. CD with gastroduodenal involvement may mimic peptic ulcer disease and can progress to gastric outlet obstruction.

Weight loss is observed more commonly in CD than in UC because of the malabsorption associated with small bowel disease. Patients may reduce their food intake in an effort to control their symptoms. Systemic symptoms are common and include fever, sweats, malaise and arthralgias. A low-grade fever may be the first warning sign of a flare. Recurrences may occur with emotional stress, infections or other acute illnesses, pregnancy, dietary indiscretions, use of cathartics or antibiotics, or withdrawal of anti-inflammatory or steroid medications.

Children may present with growth retardation and delayed or failed sexual maturation. In 10-20% of cases, patients present with extraintestinal manifestations, including arthritis, uveitis or liver disease.

Diagnosis of CD can be made endoscopically or radiologically, with contrast radiographs typically showing a cobblestone pattern to the mucosa, with areas of normal mucosa alternating with areas of inflamed mucosa ("skip lesions"). The most important pathologic feature is involvement of all layers of the bowel, not just the mucosa and the submucosa, as is characteristic of UC. Sigmoidoscopy or colonoscopy reveals that the rectum is frequently spared and right colonic predominance is common. Ninety percent of patients with CD have involvement of the terminal ileum and/or right colon. Pediatric patients are more likely (about 20%) to present with disease limited to the small intestine. Much less commonly, CD involves the more proximal parts of the gastrointestinal tract, including the mouth, tongue, esophagus, stomach and duodenum.

Strictures and obstructions in persons with CD are often inflamed and frequently resolve with medical treatment. Fixed (scarred or cicatrix) strictures may require endoscopic or surgical intervention to relieve obstructions. Fistulae and perianal disease in persons with CD may be refractory to vigorous medical treatment, including antibiotic therapy. Surgical intervention is often required for fistulae and perianal disease treatment, but both are associated with a high risk of recurrence. The risk of cancer in persons with CD may be equal to that of persons with UC if the entire colon is involved, and the risk of small intestine malignancy is increased in persons with CD, but the malignancy is as likely to arise in a previously normal area as in an inflamed area.

Prognosis for CD depends on the site and extent of disease. Periodic remissions and exacerbations are the rule. Approximately 50% of patients require surgical intervention; 50% of patients undergoing surgery require a second operation; of these patients, 50% have a third operation. Rate of recurrence is 25-50% within one year for patients who have responded to medical management. This rate is higher for patients who require surgery.

The quality of life generally is lower with CD than with UC, in part because of recurrences after surgery performed for CD. Malnutrition and chronic anemia are observed in long-standing CD. Children with CD or UC can exhibit growth retardation.

Prevalence and Incidence of IBD

IBD is observed most commonly in Northern Europe and North America. It is a disease of industrialized nations. In the U.S., approximately 1 million people have UC or CD. Before 1960, the reported incidence of UC was several times higher than that of CD. More recent data suggest that the current incidence of CD is approaching that of UC, although this change may reflect improved recognition and diagnosis of CD.

In the U.S., rates of IBD occurrence among persons of European descent have been measured, for instance, in Olmsted County, Minn. It is reported that in this population, the incidence of UC is 7.3 cases per 100,000 people per year and the prevalence is 116 cases per 100,000 people; the incidence of CD is 5.8 cases per 100,000 people per year and the prevalence is 133 cases per 100,000 people. The incidence of IBD has been reported to be highest in Ashkenazi Jews (i.e., those who have immigrated from Northern Europe), at 4-5 times that of the general population, followed by non-Jewish white populations. However, recent data suggest that incidences in non-Jewish, black, and Hispanic populations are increasing. The male-to-female ratio is approximately equal for both UC and CD. A recent study in Italy showed incidences of UC and CD similar to those in the U.S.

UC and CD are most commonly diagnosed in young adults (i.e., late adolescence to the third decade of life). The age distribution of newly diagnosed IBD cases is bell-shaped; the peak incidence occurs in people in the early part of their second decade of life, with the vast majority of new diagnoses made in people aged 15-40 years. A second smaller peak occurs in patients aged 55-65 years. However, children younger than 5 years and elderly persons are occasionally diagnosed. Only about 10% of patients with IBD are younger than 18 years. Incidence may be slightly greater in females than in males.

Medical Treatment of IBD

Care of a patient with IBD can be either medical or surgical in nature, or commonly a combination of both. Medications used for IBD are broken down into several classes based on chemical similarities of the individual agents and similarities in the mechanisms of action. The medical approach for patients with IBD is symptomatic (flaring) care and generally follows a stepwise approach to medication therapy, with progression of the medical regimen until a response is achieved. With this approach, the most benign (or temporary) drugs are used first. As they fail to provide relief, drugs from a higher step are used.

Aminosalicylates and symptomatic agents are step I drugs under this scheme; antibiotics are considered step IA drugs, given the limited situations in which they are used. Corticosteroids constitute step II drugs to be used if the step I drugs fail to adequately control the IBD. Immune modifying agents are step III drugs and are used if corticosteroids fail or are required for prolonged periods. Infliximab, a monoclonal antibody against tumor necrosis factor (TNF) $\alpha$, is also a step III drug that can be used in some situations in patients with CD and UC. Experimental agents are step IV drugs and are used only after the previous steps fail, and then are administered only by physicians familiar with their use. Drugs from all steps may be used additively; in general, the goal is to wean the patient off steroids as soon as possible to prevent long-term adverse effects from these agents. Opinions differ regarding the use of certain agents in this stepwise approach.

Step I (aminosalicylates). Oral aminosalicylate preparations available for use in the U.S. include sulfasalazine, mesalamine, balsalazide and olsalazine. Enema and suppository formulations are also available. All of these are derivatives of 5-aminosalicylic acid (5-ASA); the major differences are in the mechanism of delivery. Some of these also have unique adverse effects that other agents of this class lack. All of the aminosalicylates are useful for treating flares of IBD and for maintaining remission. None of the aminosalicylates has been proven to have greater efficacy for treatment of UC or CD over any of the others. All of them are clearly more effective in persons with UC than in persons with CD; in CD, the primarily utility is for colonic disease.

Step IA (antibiotics). The antibiotics metronidazole and ciprofloxacin are the most commonly used antibiotics in IBD. Antibiotics are used only sparingly in UC because UC increases the risk of developing antibiotic-associated pseudomembranous colitis. However, in CD, antibiotics are used for a variety of indications, most commonly for perianal disease. They are also used for fistulae and inflammatory masses in the abdomen, and they may have some efficacy in treating ileitis. The antibiotics have potential adverse effects, including nausea, anorexia, diarrhea, monilial (candidal) infections and, in the case of metronidazole, peripheral neuropathy.

Step II (corticosteroids). Corticosteroids are rapid-acting anti-inflammatory agents used in treatment of IBD for acute flares of disease only; corticosteroids have no role in maintenance of remission. Corticosteroids may be administered by a variety of routes depending on the location and severity of disease; for example they may be administered intravenously (e.g., methylprednisolone, hydrocortisone), orally (e.g., prednisone, prednisolone, budesonide, dexamethasone), or topically (enema, suppository or foam preparations).

Intravenous corticosteroids are often used for patients who are severely ill and hospitalized. In general, once a clinical response is observed (typically within 1-2 days, occasionally longer), the dose of the intravenous corticosteroid can be tapered. Before hospital discharge, conversion to an oral corticosteroid is made; further dosage tapering can be accomplished in an outpatient setting. Again, once a clinical response is seen, the dose is tapered. Most patients who use oral corticosteroids can only occasionally tolerate a relatively rapid taper after a response is achieved; occasionally, a very prolonged steroid taper is necessary to prevent relapse. When the latter situation occurs, alternative drugs (immune modifiers or anti-TNF$\alpha$ therapy) may be used. Topical corticosteroids are used in persons with distal colonic disease in a manner similar to topical mesalamine, but typically only for active disease as topical corticosteroids have only a small role in the maintenance of remission.

The potential complications of corticosteroid use are multiple and include fluid and electrolyte abnormalities, osteoporosis, aseptic necrosis, peptic ulcers, cataracts, neurologic and endocrine dysfunctions, infectious complications, and occasional psychiatric disorders (including psychosis).

Step III (immune modifiers). The immune modifiers azathioprine and 6-mercaptopurine (6-MP) are used in patients with IBD in whom remission is difficult to maintain with aminosalicylates alone. Immune modifiers work by causing a reduction in lymphocyte count, and because of that mechanism of action, their onset of action is relatively slow (typically 2-3 months). They are used most commonly for their steroid-sparing action in persons with refractory disease; they are also used as primary treatment for fistulae and the maintenance of remission in patients intolerant of aminosalicylates.

Use of these agents mandates monitoring of blood parameters; they can cause significant neutropenia or pancytopenia that would warrant a dose reduction or discontinuation. Other adverse effects of the immune modifiers include fever, rash, infectious complications, hepatitis, pancreatitis and bone marrow depression. The most common reason for discontinuing immune modifiers within the first few weeks is development of abdominal pain; occasionally, a biochemically demonstrable pancreatitis occurs. Concerns have been raised about development of malignancy in patients taking azathioprine and 6-MP.

Infliximab is an additional step III agent that works by a different mechanism. Infliximab is an anti-TNF$\alpha$ monoclonal antibody that is currently U.S. Federal Drug Administration (FDA) approved for both UC and CD, although it does appear to have a higher efficacy rate in CD. Infliximab is generally administered as infusions of 5 mg/kg for treatment of moderate to severe IBD. It is administered as 3 separate infusions of 5 mg/kg at weeks 0, 2, and 6, often followed by doses every 8 weeks for maintenance of remission. For CD, the response rate is 80% and the induction of remission rate is 50% after a single dose; with multiple dosing, higher rates of remission are attained. For UC, the response rates are 50-70%. Infliximab is also indicated for treatment of fistulizing CD; for this indication, the fistula responds (closes) in 68% of patients treated with infliximab, although 12% develop an abscess. The response can be maintained by continuing regular dosing (i.e., every 8 weeks) after the induction dose.

Infliximab treatment is extremely expensive and may also involve adverse effects, commonly including hypersensitivity and flu-like symptoms. Rare instances of lupus-like reactions and lymphoproliferative malignancies have been reported, although whether the malignancies are related to the drug or to the underlying disease process remains uncertain.

Step IV (experimental treatments). Experimental agents used in CD include methotrexate (12.5-25 mg/week orally or intramuscularly), thalidomide (50-300 mg/day orally), and interleukin 11 (1 mg/week subcutaneously). Experimental agents used in UC include cyclosporin A at a dose of 2-4 mg/kg/day intravenously (measure level; convert to oral dosing at 2-3 times the intravenous dose), nicotine at 14-21 mg/day via topical patch, butyrate enema (100 ml per rectum twice daily), and heparin (10,000 U subcutaneously twice daily). Multiple contraindications, interactions and precautions are associated with these drugs.

Chronic Gastritis

Chronic gastritis, a chronic inflammation of the stomach mucosa, is most often caused by infection with the bacterium *Helicobacter pylori*, but may also be caused by nonsteroidal anti-inflammatory drug (NSAID) use, autoimmunity, allergy, or other factors. Infectious gastritis is usually treated with multiple drug therapy, comprising an antibiotic to eliminate the underlying infection, and one or more drugs to treat the inflamed mucosa. Current drugs, used either with antibiotics to treat infective gastritis or alone to treat other forms of gastritis, are of two main classes: proton-pump inhibitors and H2-receptor blockers, both of which act by inhibiting gastric acid secretion. However, in many cases these methods are ineffective or not completely effective, and new modalities of treatment are needed.

BACKGROUND OF THE INVENTION

Inflammatory activity in IBD is known to involve activation of nuclear factor κB (NF-κB). See, e.g., Schreiber et al. (1998) *Gut* 42:477-484, concluding that, in both IBDs, but particularly CD, increased activation of NF-κB may be involved in regulation of the inflammatory response, and that inhibition of NF-κB activation may represent a mechanism by which steroids exert an anti-inflammatory effect in IBD.

Further, the anti-TNFα antibody infliximab, which can be an effective treatment for IBD, has been reported to decrease NF-κB activity, at least in CD (see Guidi et al. (2005) *Int. J. Immunopathol. Pharmacol.* 18(1):155-164).

Conversely, an increase in NF-κB activity has been reported to precede relapse of symptoms in CD patients exhibiting failure to maintain response to infliximab (see Nikolaus et al. (2000) *Lancet* 356(9240):1475-1479).

The NF-κB signaling pathway is involved in a wide range of pro-inflammatory effects. See, e.g., Schreiber et al. (1998), supra. Angiotensin II (AII), a member of the renin-angiotensin system (RAS) and the primary product of angiotensin converting enzyme (ACE), is known to exert pro-inflammatory effects in a variety of tissues, via its type 1 and type 2 receptors ($AT_1$ and $AT_2$ respectively) and, in many cases, ultimately through activation of NF-κB, as indicated below.

In the classical pathway of AII synthesis in the circulating RAS, the precursor of AII is angiotensinogen, which is principally produced in the liver and then cleaved by renin to form angiotensin I (AI), which is converted by ACE into AII that is carried to various target cells via the circulatory system. See, e.g., Inokuchi et al (2005) *Gut* 54:349-356, and sources cited therein. In addition, tissue-specific renin-angiotensin systems have been identified in many organs, suggesting that various tissues have the ability to synthesize AII independently of circulating RAS, including kidney, brain, aorta, adrenal gland, heart, stomach and colon.

Donoghue et al. (2000) *Circ. Res.* 87:1-9 reported identification of a carboxypeptidase related to ACE from sequencing of a human heart failure ventricle cDNA library. This carboxypeptidase, ACE2, was stated to be the first known human homolog of ACE. The authors further reported that the metalloprotease catalytic domains of ACE2 and ACE are 42% identical, and that, in contrast to the more ubiquitous ACE, ACE2 transcripts are found only in heart, kidney, and testis in the 23 human tissues examined.

U.S. Pat. No. 6,194,556 to Acton et al. discloses novel genes encoding ACE2. Therapeutics, diagnostics and screening assays based on these genes are also disclosed.

Harmer et al. (2002) *FEBS Lett.* 532:107-110 reported quantitative mapping of the transcriptional expression profile of ACE2 (and the two isoforms of ACE) in 72 human tissues. The study reportedly confirmed that ACE2 expression is high in renal and cardiovascular tissues. It was further reported that ACE2 shows comparably high levels of expression in the gastrointestinal system, in particular in ileum, duodenum, jejunum, cecum and colon. The authors proposed that in probing functional significance of ACE2, some consideration should be given to a role in gastrointestinal physiology and pathophysiology.

Rice et al. (2003) *Bull. Br. Soc. Cardiovasc. Res.* 16(2):5-11 reviewed potential functional roles of ACE2 and indicated that its expression is mainly localized in testis, kidney, heart and intestines.

Ferreira & Santos (2005) *Braz. J. Med. Biol. Res.* 38:499-507 have summarized important pathways of the RAS, including roles of ACE and ACE2, as shown in FIG. 1 herein.

As evidence of implication of angiotensin II, the main product of ACE, in a variety of pro-inflammatory effects, see for example:

a Phillips & Kagiyama (2002) *Curr. Opin. Investig. Drugs* 3(4):569-577, who reviewed literature showing angiotensin II to be a key factor, via nuclear factor KB (NF-κB) activation, in promoting inflammation, inter alia, in atherosclerosis;

Costanzo et al (2003) *J. Cell Physiol.* 195(3):402-410, who reported up-regulation by angiotensin II of endothelial cell adhesion molecules involved in atherosclerosis, via inflammatory cytokines through NF-κB activation;

Sanz-Rosa et al (2005) *Am. J. Physiol. Heart Circ. Physiol.* 288:$H_{111}$-H115, who reported that blocking the $AT_1$ receptor reduces the level of vascular and circulating inflammatory mediators such as NF-κB and TNF-α in spontaneous hypertension;

Esteban et al. (2004) *J. Am. Soc. Nephrol.* 15:1514-1529, who reported that angiotensin II, via $AT_1$ and $AT_2$, activates NF-κB and thereby promotes inflammation in obstructed kidney; and Inokuchi et al. (2005), supra, who reported that in angiotensinogen gene knockout mice, which have low levels of angiotensin II, inflammatory colitis induced by 2,4,6-trinitrobenzenesulfonic acid (TNBS) is ameliorated, and that blocking the $AT_1$ receptor also ameliorated TNBS-induced colitis.

Antagonism of the RAS has been postulated as a prophylactic strategy for immune mediated inflammatory bowel disease (Inokuchi et al. (2005), supra).

The proinflammatory effects of the ACE product angiotensin II have been found to be generally counterbalanced by ACE2 in various studies involving ACE2 disruption and/or mutants lacking the ACE2 gene. See for example:

Crackower et al. (2002) *Nature* 417(6891):822-828, who reported that disruption of ACE2 or deletion of the ACE2 gene in various rat models raises the level of angiotensin II;

Huentelman et al. (2005) *Exp. Physiol.* 90(5):783-790, who reported that injection of a vector encoding ACE2 protects wild-type mice against angiotensin II induced cardiac hypertrophy and fibrosis; and Imai et al. (2005) *Nature* 436(7047):112-116, who reported that deletion of the ACE gene or giving ACE2 protein to wild-type mice protects against acid-induced acute lung injury.

The primary product of ACE2, namely angiotensin (1-7), via its receptor (Mas), has generally been found to oppose functions of the ACE product angiotensin II. See for example:

Guy et al. (2005) *Biochim. Biophys. Acta* 1751(1):2-8, who reviewed literature indicating inter alia that ACE2 regulates heart and kidney function by control of angiotensin II levels relative to angiotensin (1-7), and may therefore counterbalance the effects of ACE within the RAS;

Ferreira & Santos (2005), supra, who reviewed literature indicating inter alia that ACE inhibitor benefits may be partly mediated by the ACE2 product angiotensin (1-7), plasma levels of which are greatly increased following chronic administration of ACE inhibitors;

Mendes et al. (2005) *Regul. Pept.* 125(1-3):29-34, who reported that infusion of angiotensin (1-7) reduces angiotensin II levels in the heart and postulated that such reduction may contribute to beneficial effects of angiotensin (1-7); and Tallant & Clark (2003) *Hypertension* 42:574-579, who reported that angiotensin (1-7) reduces smooth muscle growth after vascular injury, and counteracts stimulation by angiotensin II of growth and mitogen activated protein (MAP) kinase activity in rat aortic vascular smooth muscle cells.

Thus low levels of angiotensin II appear to ameliorate inflammatory colitis (Inokuchi et al. (2005), supra), and ACE2 activity appears to counterbalance inflammatory effects of angiotensin II in a variety of tissues, whether by increasing angiotensin (1-7) levels or reducing angiotensin II levels or both.

In one scenario, therefore, promotion of ACE2 activity might be of interest for reducing inflammation in diseases such as IBD. Huentelman et al (2004) *Hypertension* 44:903-906 proposed, similarly, that in vivo activation of ACE2 could lead to protection and successful treatment for hypertension and other cardiovascular diseases, by counterbalancing the potent vasoconstrictive effects of angiotensin II.

Above-cited U.S. Pat. No. 6,194,556, which discloses novel genes encoding ACE2, proposes at column 60, lines 36-54 that: "Yet other diseases or conditions in which bradykinin is overproduced and in which ACE-2 agonist therapeutics capable of inactivating bradykinin can be useful include pathological conditions such as septic and hemorrhagic shock, anaphylaxis, arthritis, rhinitis, asthma, inflammatory bowel disease, sarcoidosis, and certain other conditions including acute pancreatitis, post-gastrectomy dumping syndrome, carcinoid syndrome, migraine, and hereditary angioedema" (references omitted).

Agents that inhibit rather than promote ACE2 activity have been described in the art. For example, Huentelman et al. (2004), supra, reported efforts to identify ACE2 inhibitory compounds that inhibit infection by SARS-CoV, the coronavirus responsible for severe acute respiratory syndrome (SARS), for which ACE2 has been found to be a functional receptor. Among the compounds so identified was NAAE (N-(2-aminoethyl)-1-aziridine-ethanamine).

U.S. Pat. No. 6,900,033 to Parry et al. discloses peptides comprising specific amino acid sequences that are said to specifically bind to ACE2 protein or ACE2-like polypeptides. It is proposed at column 53, lines 63-65 thereof that "an abnormally high a[n]giotensin II level could result from abnormally low activity of ACE-2" and at column 63, lines 21-32 thereof that "ACE-2 binding polypeptides . . . which activate ACE-2-induced signal transduction can be administered to an animal to treat, prevent or ameliorate a disease or disorder associated with aberrant ACE-2 expression, lack of ACE-2 function, aberrant ACE-2 substrate expression, or lack of ACE-2 substrate function. These ACE-2 binding polypeptides may potentiate or activate either all or a subset of the biological activities of ACE-2-mediated substrate action . . . ".

Further, at column 71, lines 26-37 thereof, polypeptides "of the invention" (whether activating or inhibitory not specified) inter alia are said to be useful "to treat, prevent, or ameliorate inflammation, including, but not limited to, inflammation associated with infection (e.g., septic shock, sepsis, or systemic inflammatory response syndrome (SIRS)), ischemia-reperfusion injury, polytrauma, pain, endotoxin lethality, arthritis (e.g., osteoarthritis and rheumatoid arthritis), complement-mediated hyperacute rejection, nephritis, cytokine or chemokine induced lung injury, inflammatory bowel disease, Crohn's disease, and resulting from over production of cytokines (e.g., TNF or IL-1)." Separately, ACE2 binding peptides that are reported to inhibit ACE2 in vitro are identified in Table 2 at columns 127-130 thereof.

Huang et al. (2003) *J. Biol. Chem.* 278(18):15532-15540 reported that one such ACE2 inhibitory peptide, namely DX600, exhibited an ACE2 $K_i$ value of 2.8 nM.

Li et al. (2005) *Am. J. Physiol. Renal Physiol.* 288:F353-F362 reported that DX600 blocked angiotensin I mediated generation of angiotensin (1-7) in rat nephron segments.

U.S. Pat. No. 6,632,830 to Acton et al. discloses compounds comprising a zinc coordinating moiety and an amino acid mimicking moiety, said to be useful for modulating activity of ACE2. More particularly, there are disclosed ACE2 inhibiting compounds of a generic formula presented therein. Such compounds are said to be useful for treating an "ACE-2 associated state" in a patient. "ACE-2 associated states" are said to include high blood pressure and diseases and disorders related thereto, in particular arterial hypertension, congestive heart failure, chronic heart failure, left ventricular hypertrophy, acute heart failure, myocardial infarction and cardiomyopathy; states associated with regulating smooth cell proliferation, in particular smooth muscle cell proliferation; kidney diseases and disorders; other hyperadrenergic states; kinetensin associated conditions including those caused by, or contributed to by, abnormal histamine release, for example in local or systemic allergic reactions including eczema, asthma and anaphylactic shock; infertility or other disorders relating to gamete maturation; cognitive disorders; disorders associated with bradykinin and des-Arg bradykinin; and "other examples" (column 36, lines 58-67 thereof) that are said to include "SIRS . . . , sepsis, polytrauma, inflammatory bowel disease, acute and chronic pain, bone destruction in rheumatoid and osteo arthritis and periodontal disease, dysmenorrhea, premature labor, brain edema following focal injury, diffuse axonal injury, stroke, reperfusion injury and cerebral vasospasm after subarachnoid hemorrhage, allergic disorders including asthma, adult respiratory distress syndrome, wound healing and scar formation."

Dales et al. (2002) *J. Am. Chem. Soc.* 124:11852-11853 reported ACE2 $IC_{50}$ values of a range of such compounds. The most active of these was compound 16, identified therein as having the formula

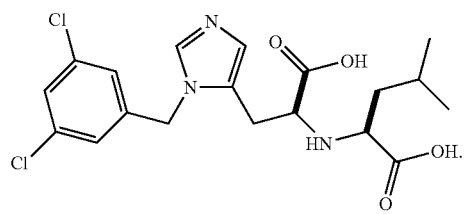

All four stereoisomers of compound 16 were prepared, and the greatest potency was reported for the S,S-isomer, which reportedly had an IC$_{50}$ for ACE2 of 0.44 nM. The S,S-isomer of the above compound, 2-[1-carboxy-2-[3-(3,5-dichlorobenzyl)-3H-imidazol-4-yl]-ethylamino]-4-methylpentanoic acid, is referred to herein as GL1001 and has previously been referred to as MLN-4760.

U.S. Patent Application Publication No. 2004/0082496 of Acton et al discloses additional compounds said to be useful for modulating activity of ACE2. Methods of using the inhibitors and pharmaceutical compositions containing the inhibitors to treat a body weight disorder, to decrease appetite, to increase muscle mass, to decrease body fat, to treat diabetes and to treat a state associated with altered lipid metabolism, are also described.

As indicated above, existing pharmacotherapies for IBD and chronic gastritis have drawbacks including one or more of poor or unreliable efficacy, adverse side effects and high cost. There remains a need for additional pharmacotherapies for inflammatory diseases of the digestive tract such as IBD and chronic gastritis, more particularly for either or both of UC and CD, to extend the range of options available to the prescribing physician and the IBD or chronic gastritis patient.

SUMMARY OF THE INVENTION

There is now provided a method for treating an inflammatory disease of the digestive tract in a subject, comprising administering to the subject a therapeutically effective amount of a compound selected from the group consisting of GL1001, pharmaceutically acceptable salts thereof and prodrugs thereof.

Beneficial effects of such treatment can include, in various embodiments:

(a) reducing or alleviating inflammation or a pathological process associated therewith or secondary thereto; and/or (b) promoting healing of mucosal ulceration.

Accordingly, there is further provided a method for reducing or alleviating inflammation or a pathological process associated therewith or secondary thereto and/or promoting healing of mucosal ulceration in a subject having an inflammatory disease of the digestive tract, comprising administering to the subject a therapeutically effective amount of a compound selected from the group consisting of (S,S)-2-[1-carboxy-2-[3-(3,5-dichlorobenzyl)-3H-imidazol-4-yl]-ethylamino]-4-methylpentanoic acid, pharmaceutically acceptable salts thereof and prodrugs thereof.

There is still further provided a method for inducing or maintaining remission of an inflammatory disease of the digestive tract in a subject, comprising administering to the subject a therapeutically effective amount of a compound selected from the group consisting of GL1001, pharmaceutically acceptable salts thereof and prodrugs thereof.

According to each of the above embodiments, the inflammatory disease can be, for example, chronic gastritis.

Alternatively according to each of the above embodiments, the inflammatory disease can be, for example, IBD, more particularly UC or CD.

There is still further provided a method for avoiding corticosteroid therapy in a subject having aminosalicylate-refractory IBD, comprising administering a therapeutically effective amount of a compound selected from the group consisting of (S,S)-2-[1-carboxy-2-[3-(3,5-dichlorobenzyl)-3H-imidazol-4-yl]-ethylamino]-4-methylpentanoic acid, pharmaceutically acceptable salts thereof and prodrugs thereof, optionally in adjunctive therapy with an aminosalicylate, but in absence of corticosteroids.

There is still further provided a therapeutic combination comprising (a) a compound selected from the group consisting of GL1001, pharmaceutically acceptable salts thereof and prodrugs thereof; and (b) at least one additional agent selected from the group consisting of aminosalicylates, corticosteroids, immunosuppressants, anti-TNFα agents and combinations thereof.

Other embodiments, including particular aspects of the embodiments summarized above, will be evident from the detailed description that follows.

(From Ferreira & Santos (2005), supra.)

Figure 2:
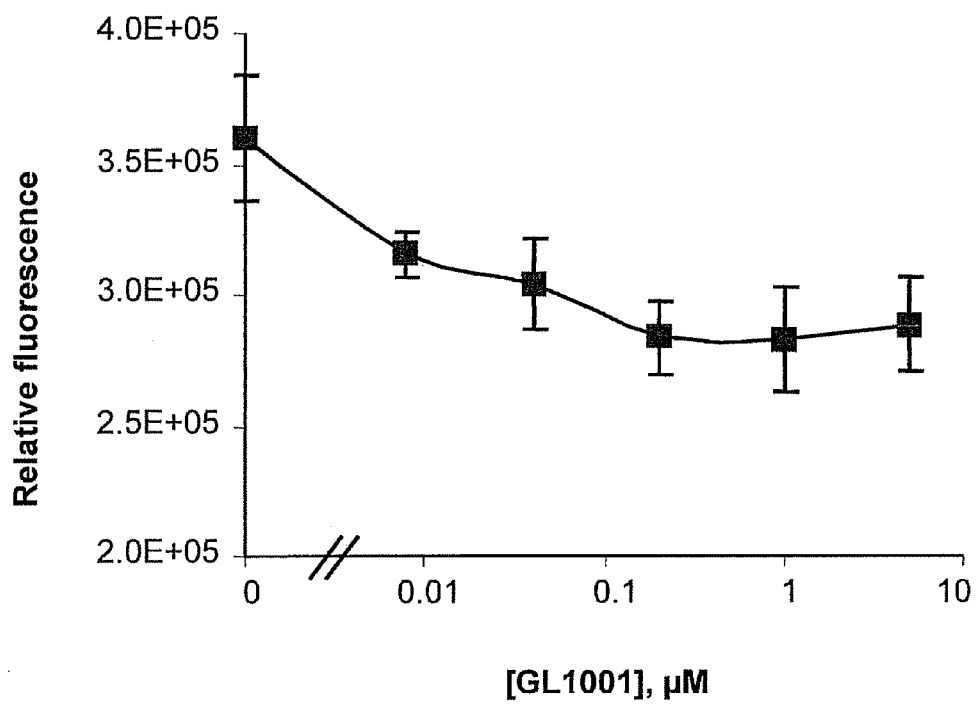

FIG. 2 is a graphical representation of inhibition by GL1001 of TNFα-induced activation of NF-κB in recombinant HeLa reporter cells, as described in Example 2.

Figure 3:
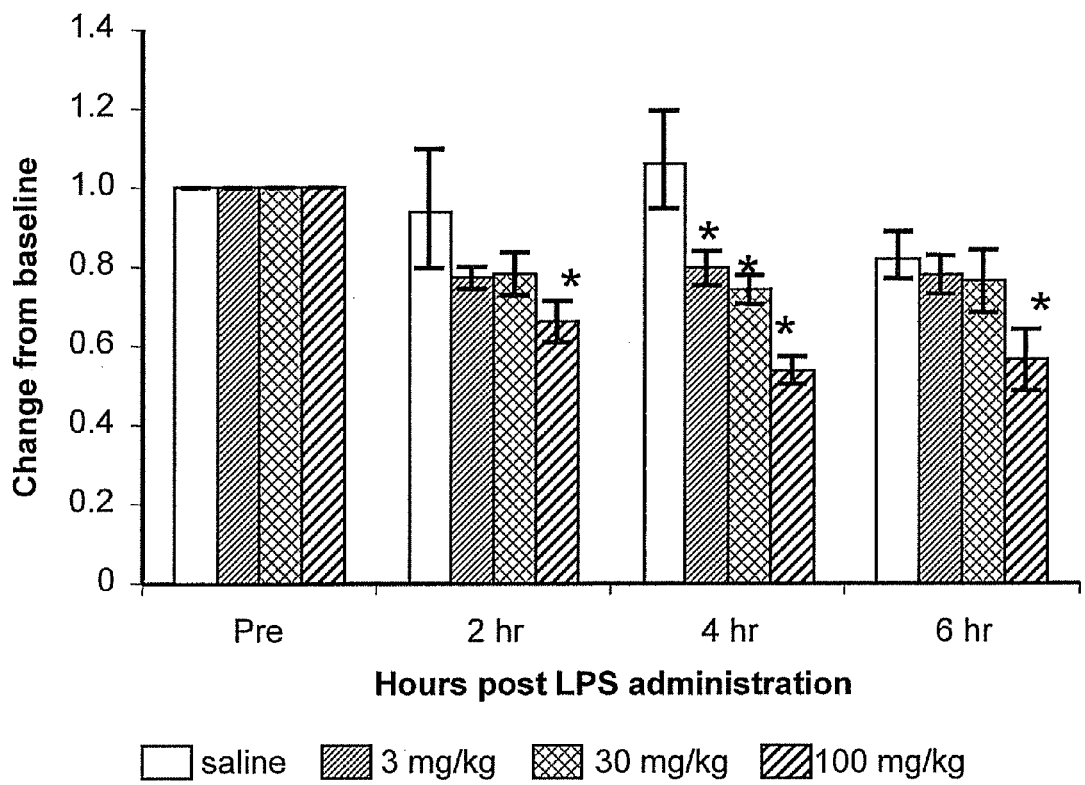

FIG. 3 is a graphical representation of inhibition by GL1001 of in vivo basal NF-κB dependent transcription in recombinant reporter mice, as described in Example 3.

Figure 4:
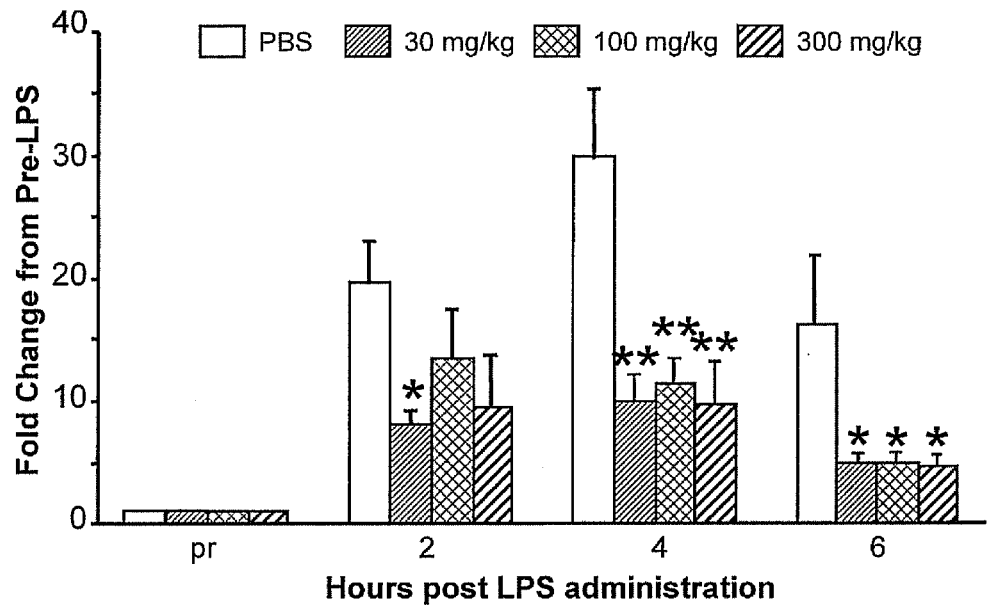

FIG. 4 is a graphical representation of inhibition by GL1001 of in vivo LPS induced NF-κB signaling in mice, as described in Example 4. Mice were pretreated with GL1001 (subcutaneous) for 1 hour before LPS treatment. All mice treated with 0.1 mg/kg LPS (i.v.). Abdominal ROI used for quantitative data (2.76×3.7 cm). Mean ±SEM, n=5 for each group; *p<0.05, **p<0.01, ANOVA and student t-test between treatments and controls.

Figure 5:
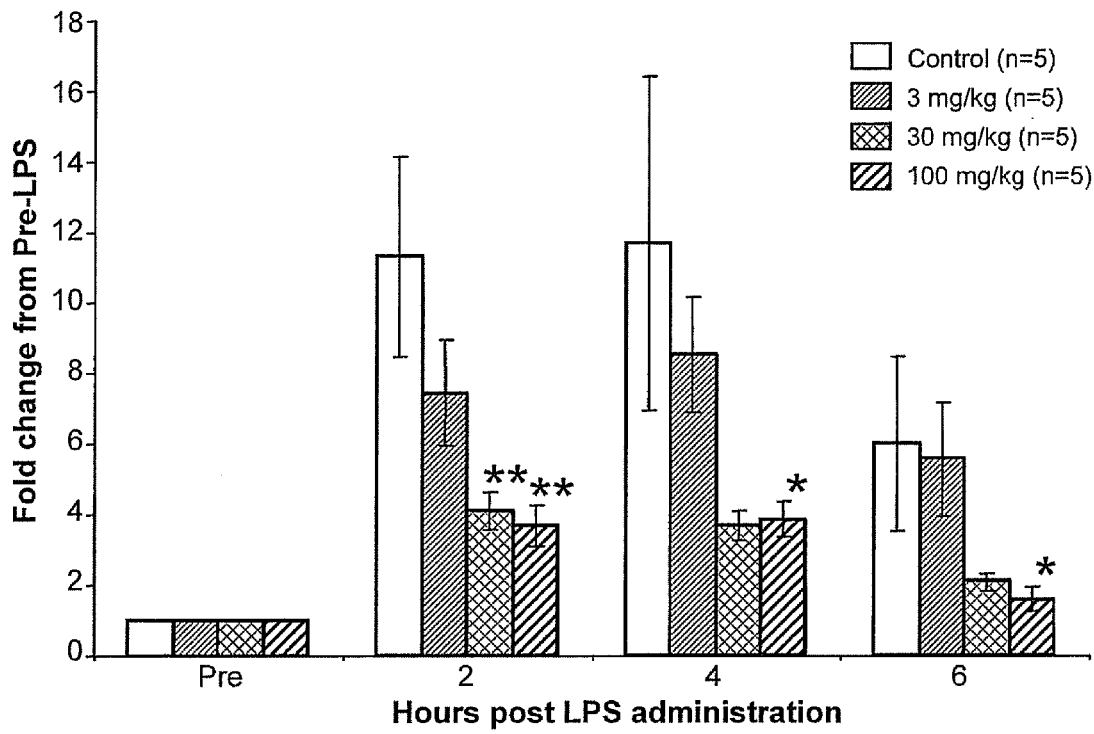

FIG. 5 is a graphical representation of inhibition by GL1001 of in vivo LPS induced NF-κB signaling in mice, as described in Example 4. Male mice were pretreated with GL1001 and LPS, and were imaged, as in FIG. 4. Mean ±SEM, n=5 for each group; *p<0.05, **p<0.01, ANOVA and student t-test between treatments and controls.

Figure 6:
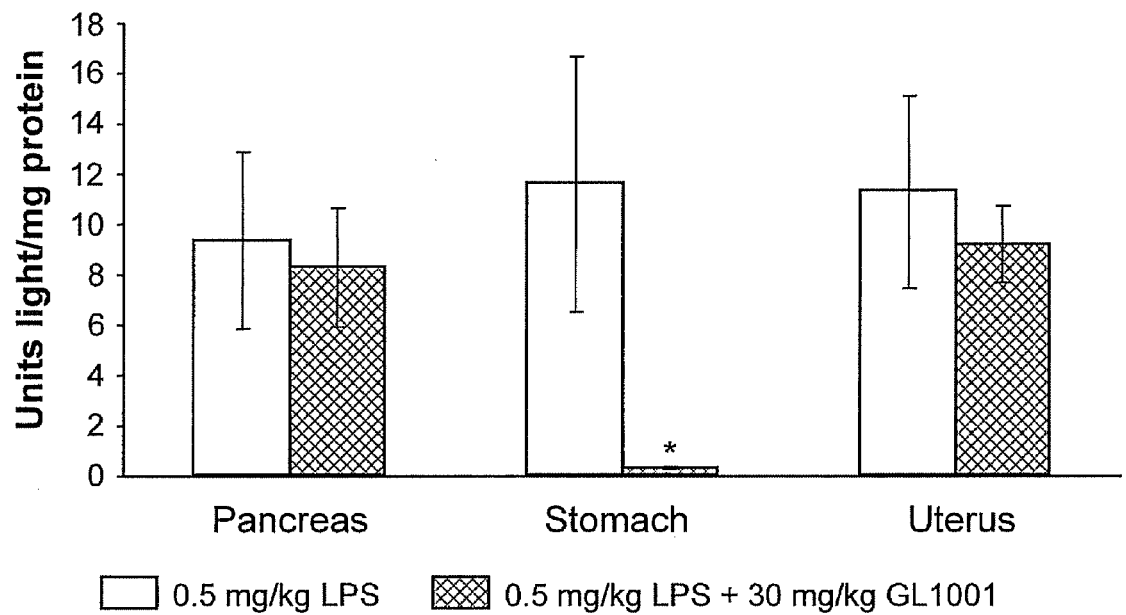

FIG. 6 is a graphical representation of inhibition by GL1001 of LPS induced NF-κB dependent transcription in selected organs of recombinant reporter mice, as described in Example 4.

Figure 7:
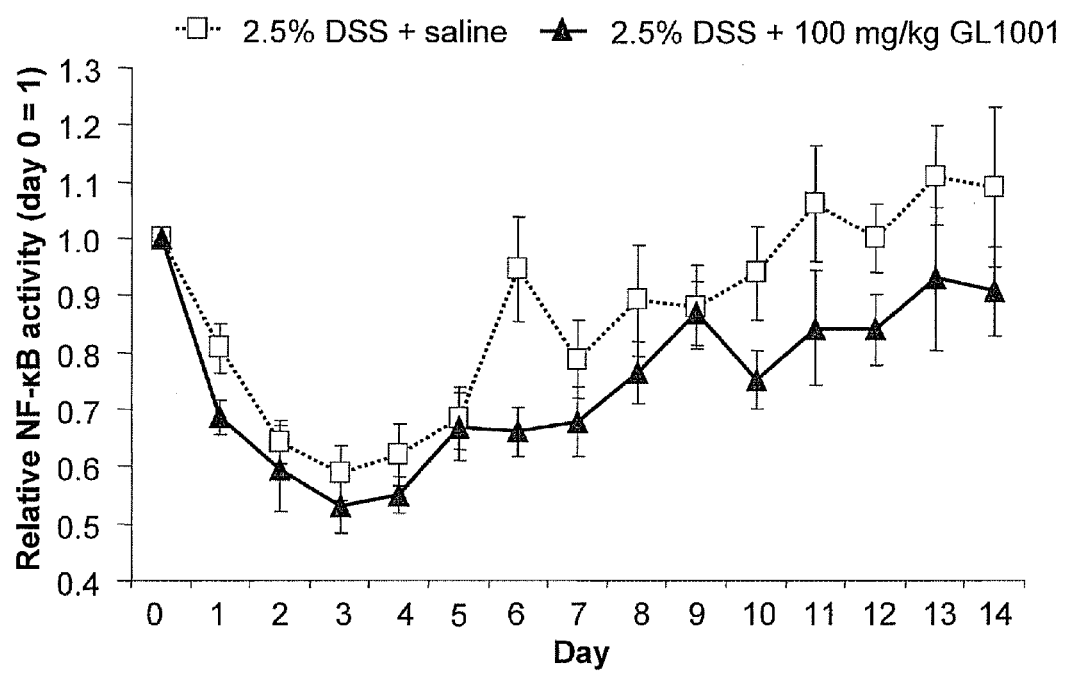

FIG. 7 is a graphical representation of results of in vivo imaging and abdominal ROI analysis. Mice were imaged using biophotonic imaging as discussed in Example 5. A region of interest encompassing the abdominal cavity was used for photon analysis. Mean ±SEM, n=4 control water group, n=10 for DSS+saline and DSS+100 mg/kg GL1001. ANOVA and student t-test were used to test for significance between the DSS+saline and DSS+GL1001 treatment groups.

Figure 8:
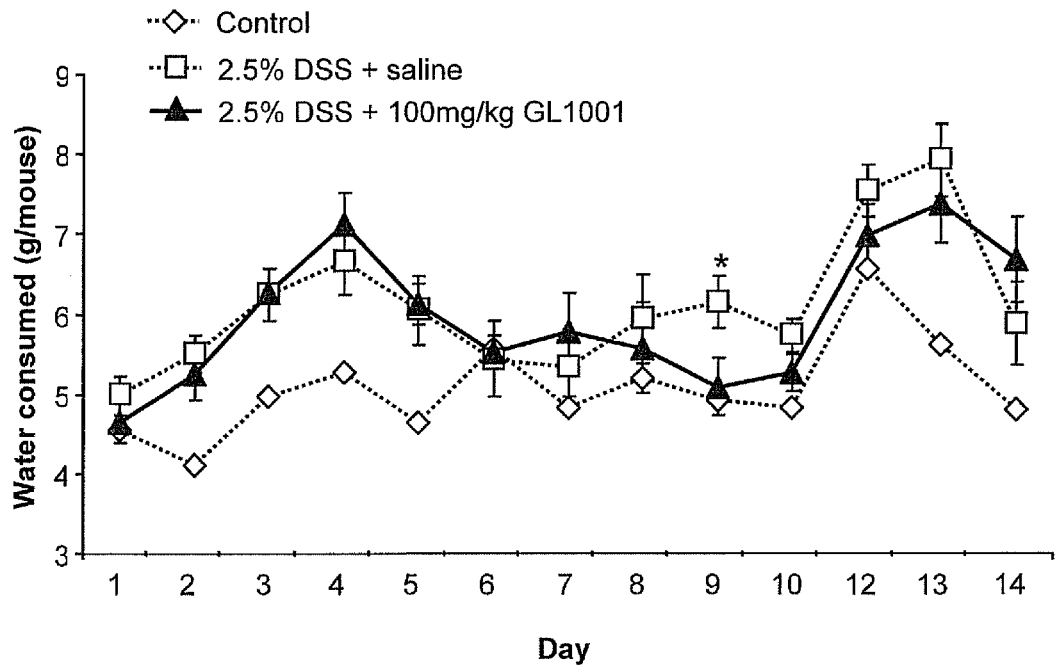

FIG. 8 is a graphical representation of results showing fluid intake per mouse. Water bottles were weighed daily and fluid consumption was represented as grams of water consumed per mouse, as described in Example 5. Mean ±SEM, n=4 control water group, n=10 for DSS+saline and DSS+100 mg/kg GL1001. ANOVA and student t-test were used to test for significance between the DSS+saline and DSS+GL1001 treatment groups; *p<0.05.

Figure 9:
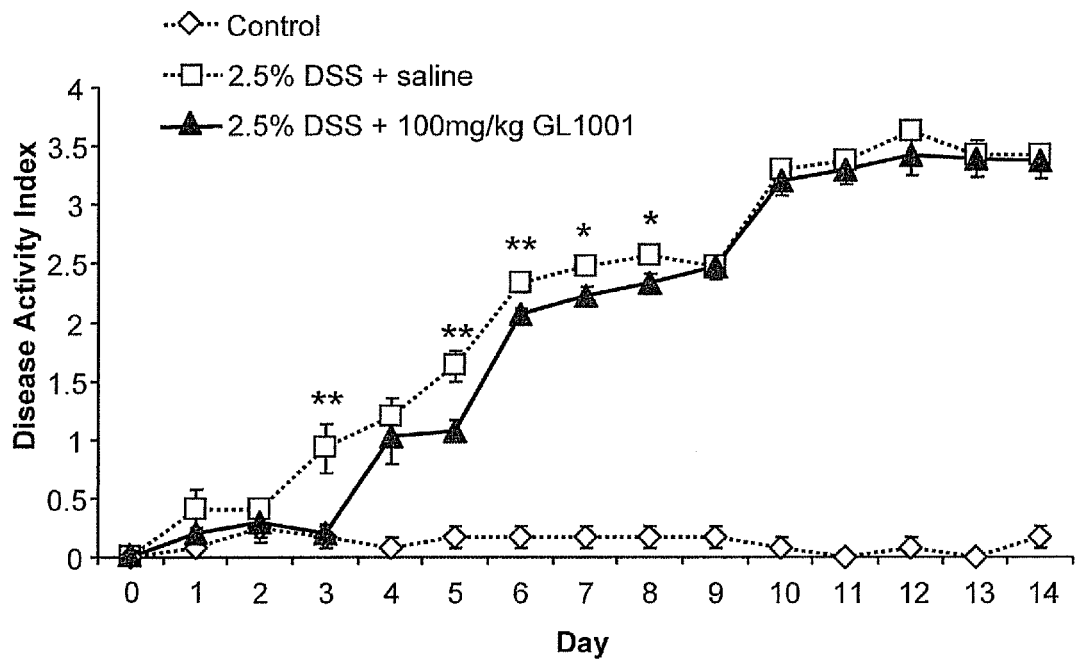

FIG. 9 is a graphical representation of results showing inhibition of IBD (as measured by IBD activity index) by GL1001. The index was determined for each mouse at each time point as described in Table 3 of Example 5. Mean ±SEM; ANOVA and student t-test were used to test for significance between the DSS+saline control and DSS+GL1001 treatment groups, *p<0.05, **p<0.01.

Figure 10:
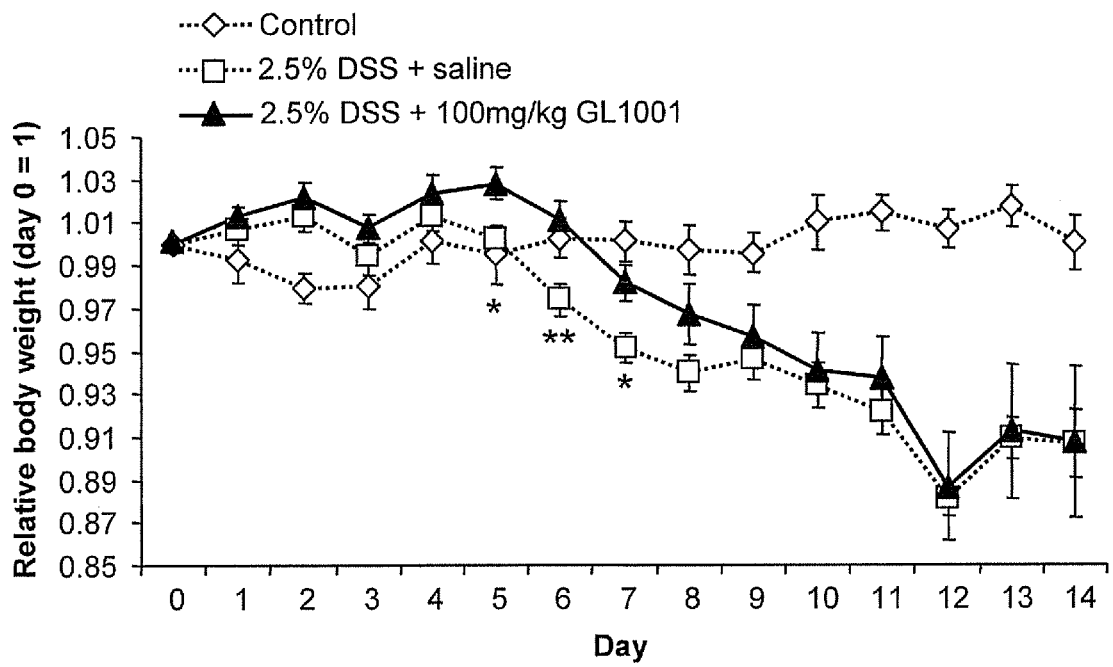

FIG. 10 is a graphical representation of results showing body weight change in response to DSS treatment, as described in Example 5. Relative body weights are shown over the time course of the experiment. Mean ±SEM; ANOVA and student t-test were used to test for significance between the DSS+saline control and DSS+GL1001 treatment groups, *p<0.05, **p<0.01.

Figure 11:
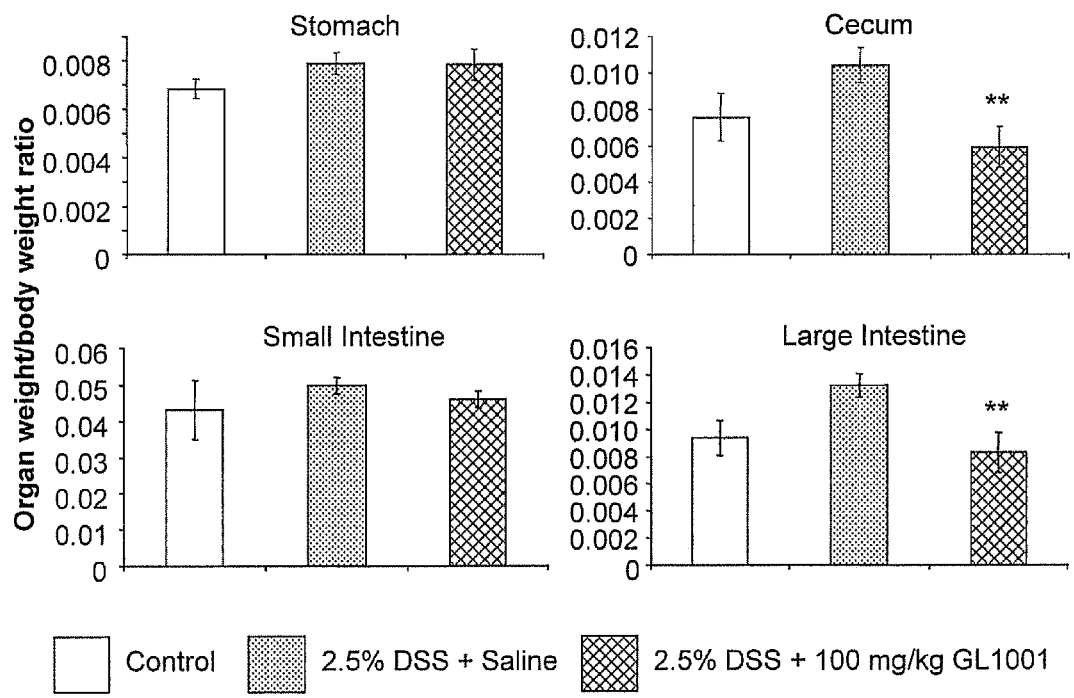

FIG. 11 is a graphical representation of organ weight/body weight ratio measurements indicating that GL1001 treated mice have a reduction in DSS induced organ weight increase as compared to DSS controls, as described in Example 5. Mean ±SEM; ANOVA and student t-test were used to test for significance between the DSS+saline control and DSS+GL1001 treatment groups, **p<0.01.

Figure 12:
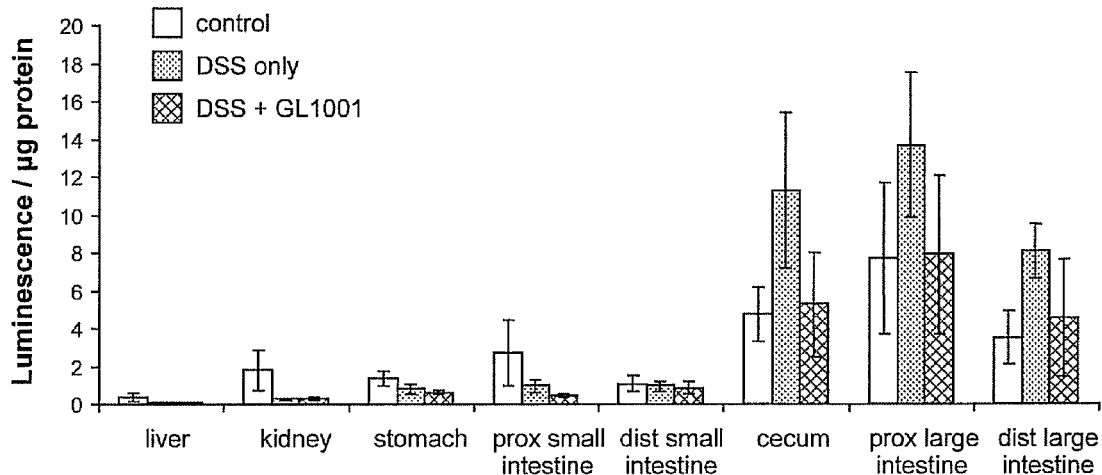

FIG. 12 is a graphical representation of results showing that cecum and large intestine demonstrate increased luciferase in the DSS control treatment group in a luciferase organ lysate analysis. Assay performed as described in Example 5. Mean ±SEM; prox=proximal, dist=distal.

Figure 13:
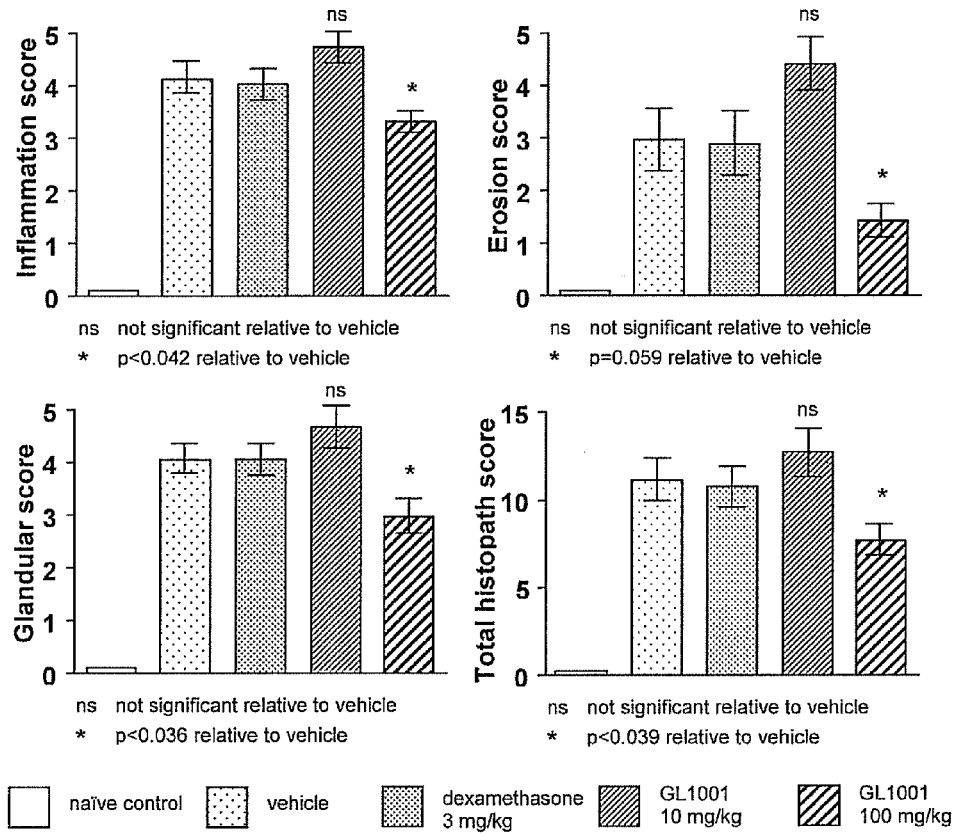

FIG. 13 is a graphical representation of results showing that once-daily subcutaneous administration of GL1001 at 100 mg/kg reduces various histopathological effects (inflammation, crypt destruction and epithelial erosion or ulceration, as measured respectively by inflammation, glandular and erosion scores on a 0-5 scale, and a total histopathological score) in distal colon of DSS-treated mice, as described in Example 6.

Figure 14:
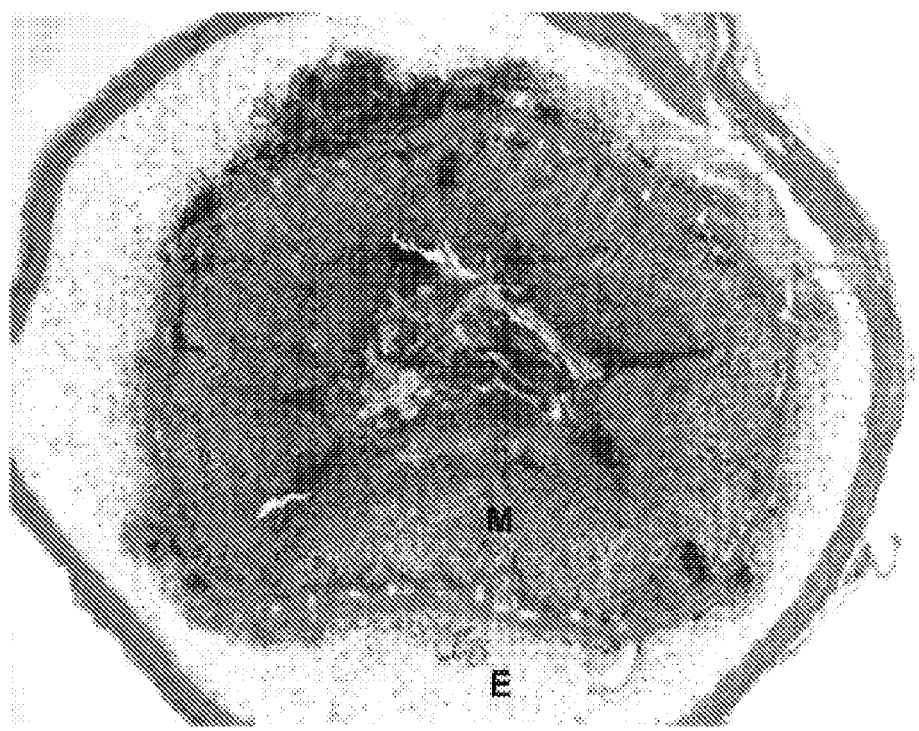
Figure 14:
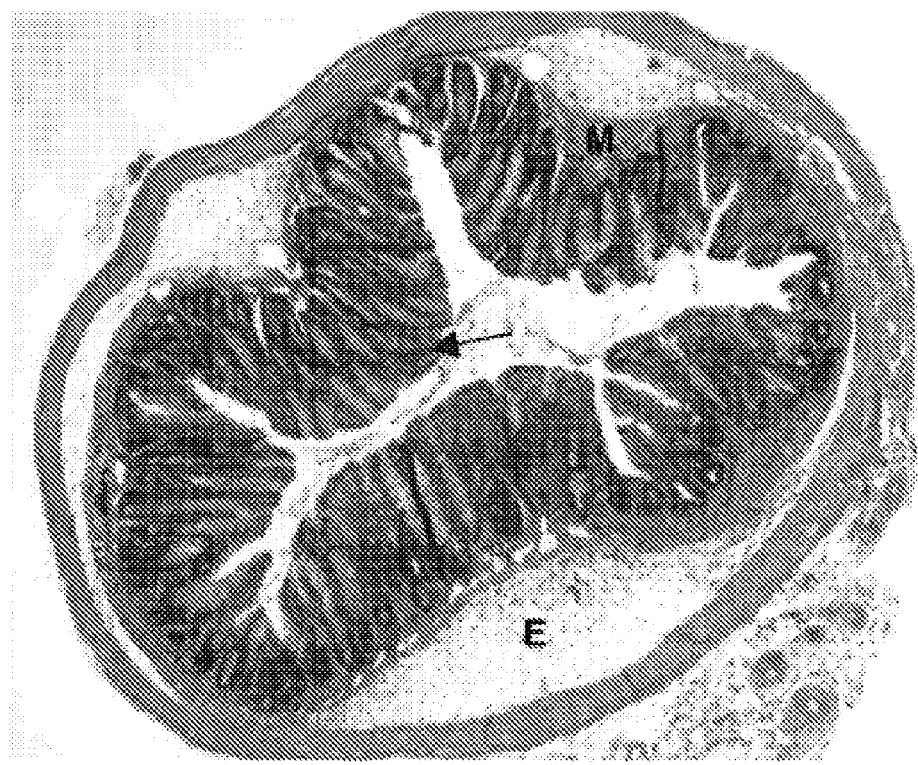

FIG. 14 presents comparative micrographs showing histological changes in distal colon of DSS-treated mice resulting from once-daily subcutaneous administration of GL1001 at 100 mg/kg, as described in Example 6.

Figure 15:
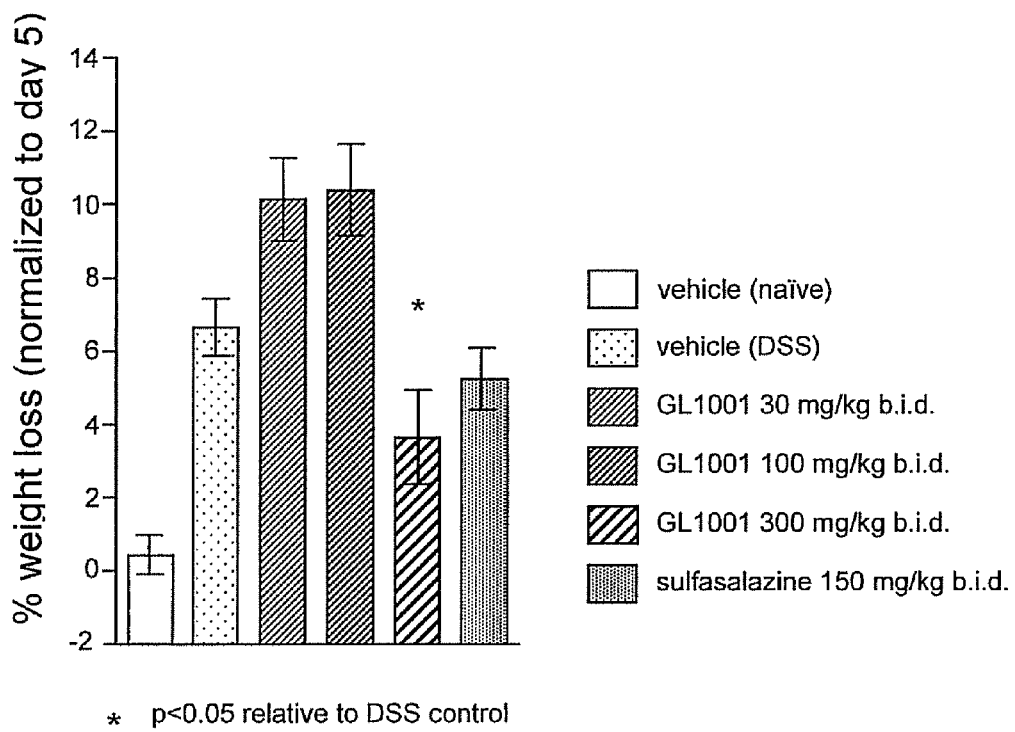

FIG. 15 is a graphical representation of results of the study of Example 7, showing that twice-daily (b.i.d.) subcutaneous administration of 300 mg/kg GL1001 reduces percentage weight loss of mice treated with DSS. No significant effect of sulfasalazine (150 mg/kg b.i.d.) is seen.

Figure 16:
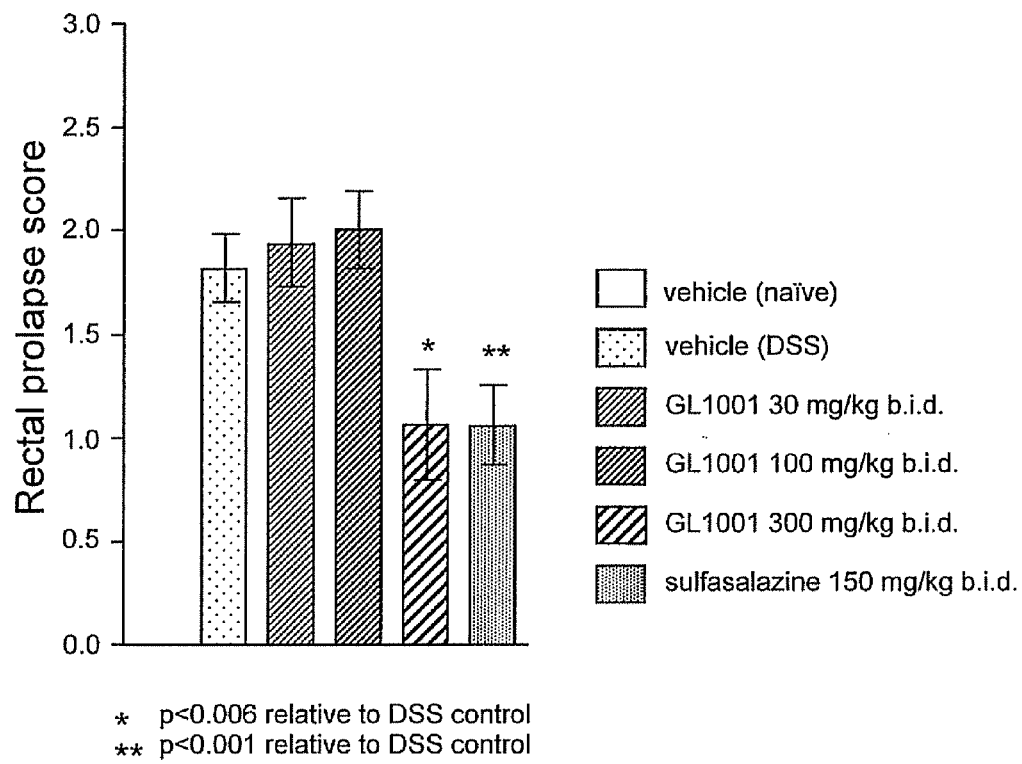

FIG. 16 is a graphical representation of results of the study of Example 7, showing that twice-daily (b.i.d.) subcutaneous administration of 300 mg/kg GL1001 or 150 mg/kg sulfasalazine reduces rectal prolapse in mice treated with DSS.

Figure 17:
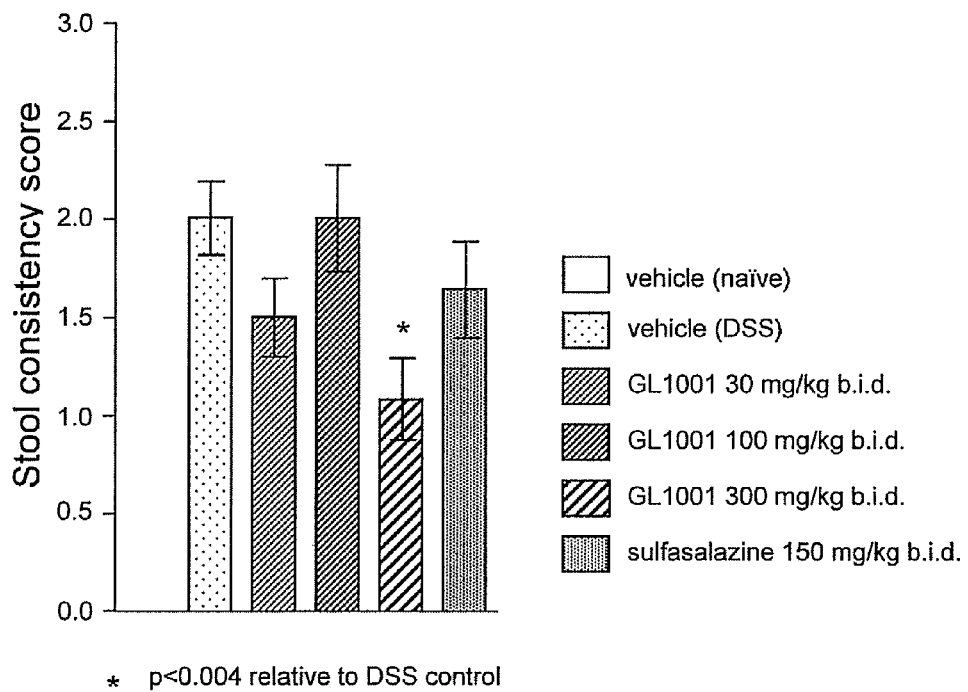

FIG. 17 is a graphical representation of results of the study of Example 7, showing that twice-daily (b.i.d.) subcutaneous administration of 300 mg/kg GL1001 reduces stool consistency in mice treated with DSS. No significant effect of sulfasalazine (150 mg/kg b.i.d.) is seen.

Figure 18:
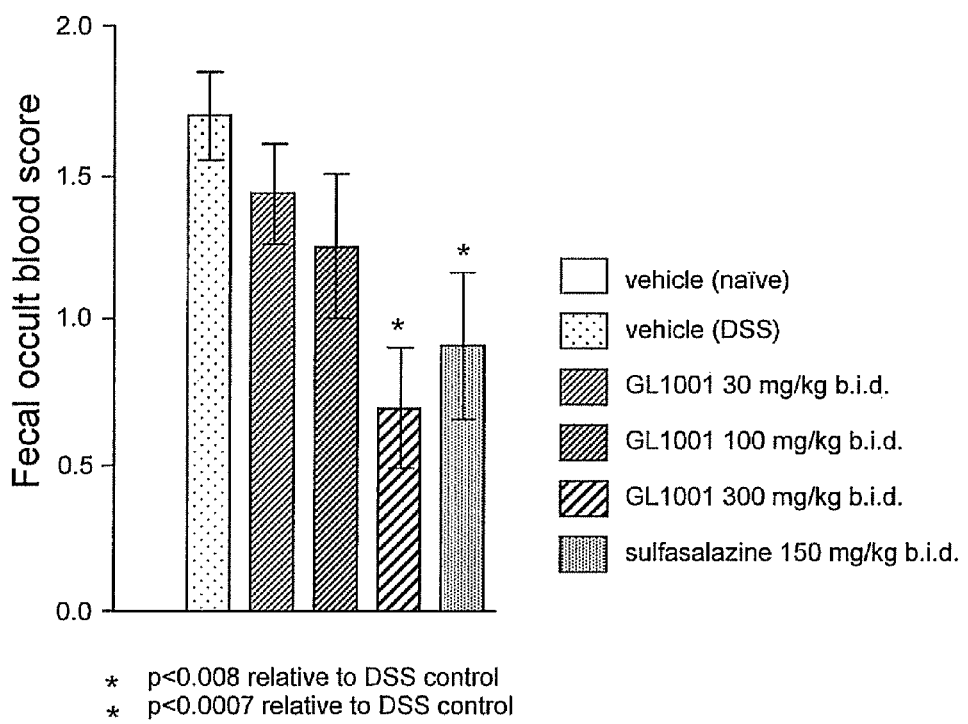

FIG. 18 is a graphical representation of results of the study of Example 7, showing that twice-daily (b.i.d.) subcutaneous administration of 300 mg/kg GL1001 or 150 mg/kg sulfasalazine reduces fecal occult blood in mice treated with DSS.

Figure 19:
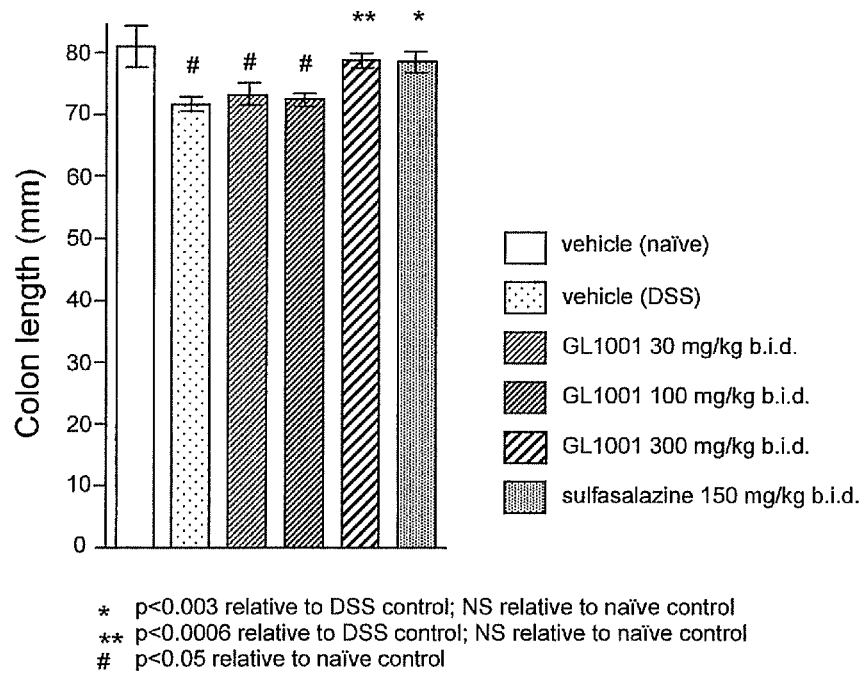

FIG. 19 is a graphical representation of results of the study of Example 7, showing that twice-daily (b.i.d.) subcutaneous administration of 300 mg/kg GL1001 or 150 mg/kg sulfasalazine inhibits reduction in colon length of mice treated with DSS.

Figure 20:
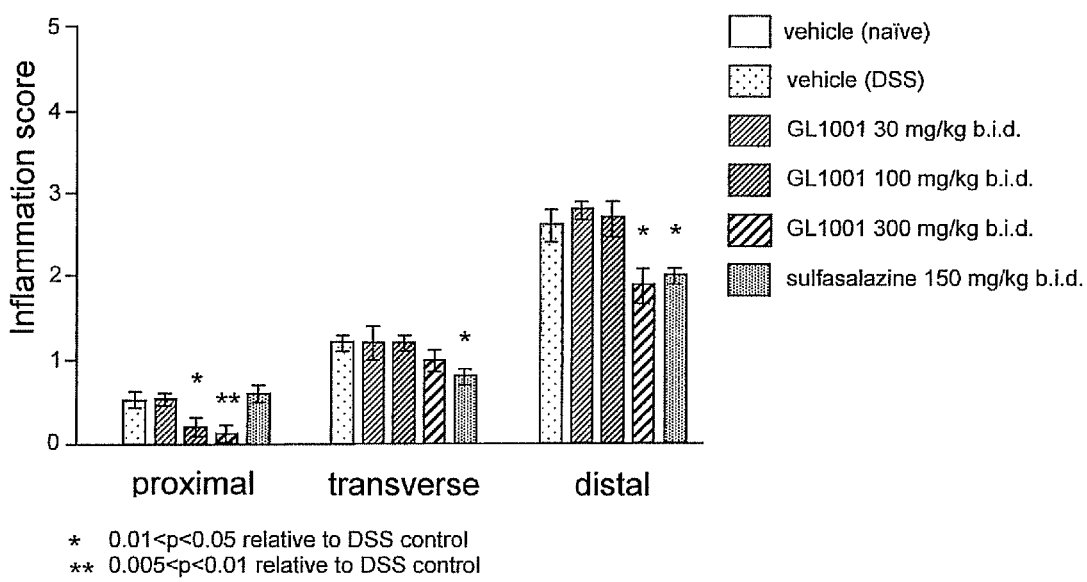

FIG. 20 is a graphical representation of results of the study of Example 7, showing that twice-daily (b.i.d.) subcutaneous administration of 300 mg/kg GL1001 or 150 mg/kg sulfasalazine reduces distal colon inflammation score in mice treated with DSS.

Figure 21:
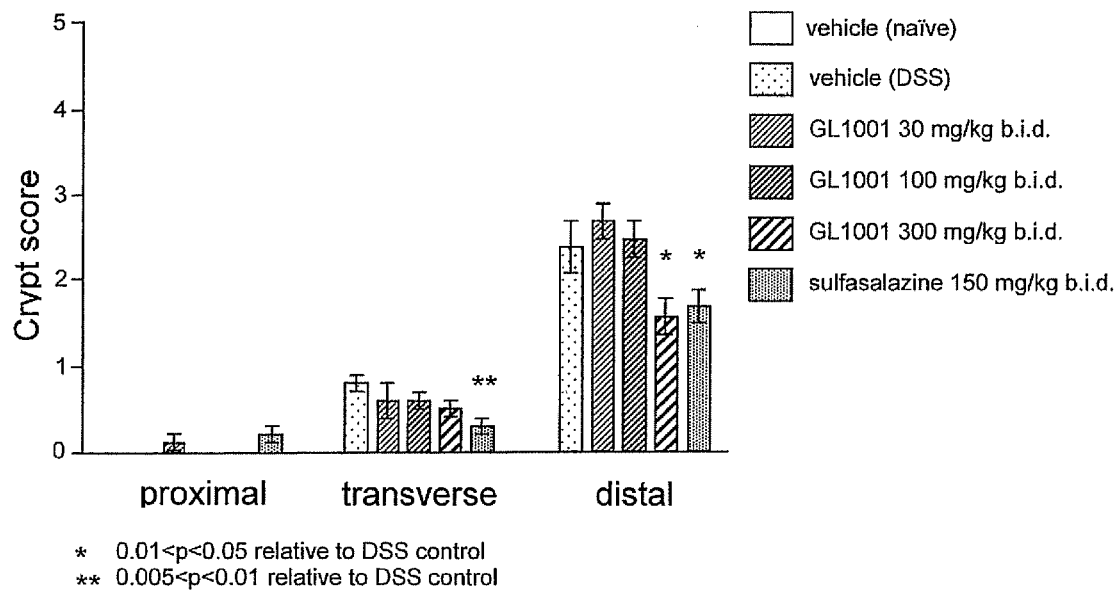

FIG. 21 is a graphical representation of results of the study of Example 7, showing that twice-daily (b.i.d.) subcutaneous administration of 300 mg/kg GL1001 or 150 mg/kg sulfasalazine reduces distal colon crypt score in mice treated with DSS.

Figure 22:
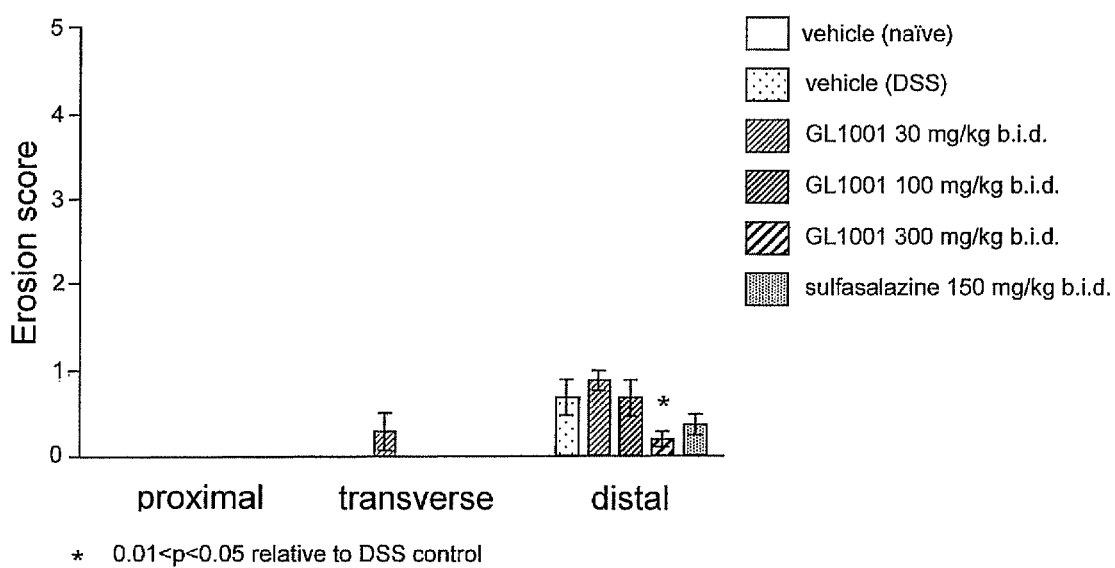

FIG. 22 is a graphical representation of results of the study of Example 7, showing that twice-daily (b.i.d.) subcutaneous administration of 300 mg/kg GL1001 reduces distal colon erosion score in mice treated with DSS.

Figure 23:
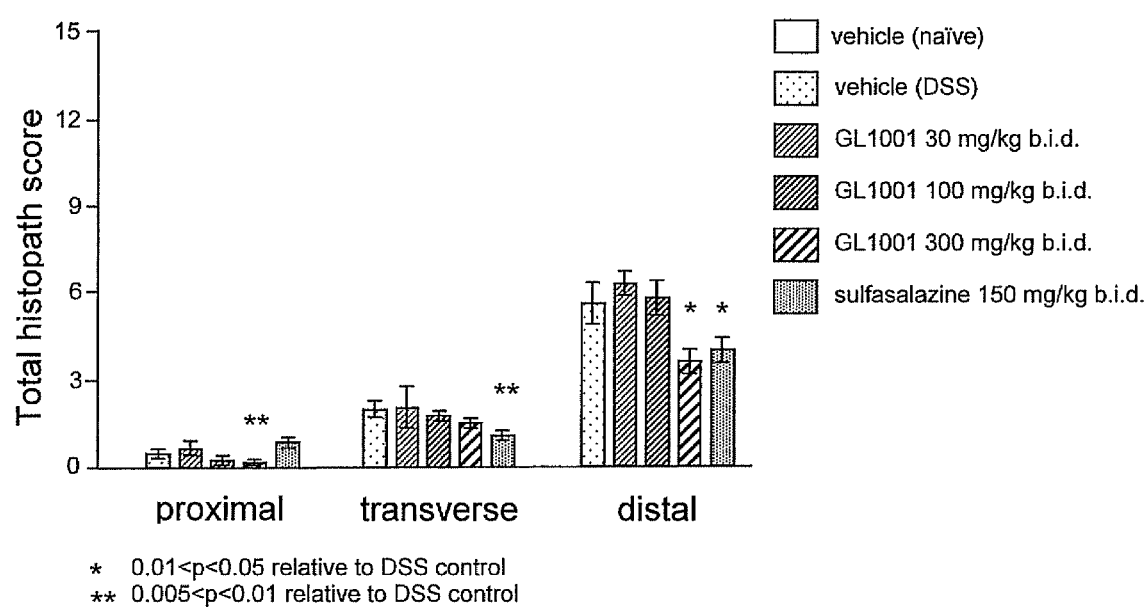

FIG. 23 is a graphical representation of results of the study of Example 7, showing that twice-daily (b.i.d.) subcutaneous administration of 300 mg/kg GL1001 or 150 mg/kg sulfasalazine reduces distal colon total histopathology score in mice treated with DSS.

DETAILED DESCRIPTION

Various therapeutic methods are described herein, all involving administration of a particular compound, or a salt or a prodrug thereof, to a subject having an inflammatory disease of the digestive tract. The particular compound according to the present invention is (S,S)-2-[1-carboxy-2-[3-(3,5-dichlorobenzyl)-3H-imidazol-4-yl]-ethylamino]-4-methylpentanoic acid, otherwise known as GL1001, and is the (S,S)-enantiomer of a compound having the formula

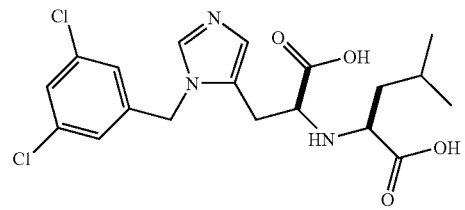

as disclosed for example by Dales et al. (2002), supra, together with a process for preparing such a compound. In brief, this process comprises treating (S)-histidine methyl ester with Boc$_2$O to provide a fully protected histidine derivative. The N-3 imidazole nitrogen is then selectively alkylated using the triflate of 3,5-dichlorobenzyl alcohol. Following Boc deprotection, reductive amination between the resulting alkylated histidine derivative and a β-ketoester furnishes a diester amine compound, which by hydrolysis yields 2-[1-carboxy-2-[3-(3,5-dichlorobenzyl)-3H-imidazol-4-yl]-ethylamino]-4-methylpentanoic acid as a mixture of diastereomers. The diastereomers can be separated and purified using HPLC and crystallization.

Other processes can be used to prepare GL1001, including without limitation processes described in above-referenced U.S. Pat. No. 6,632,830 and U.S. Published Patent Application No. 2004/0082496.

Methods provided herein are useful in treating inflammatory diseases of the whole or any part or parts of the digestive tract of a subject. In particular, the present methods are useful in treating chronic gastritis and IBD, including UC and CD.

A "subject" herein is a warm-blooded animal, generally a mammal such as, for example, a cat, dog, horse, cow, pig, mouse, rat or primate, including a human. In one embodiment the subject is human, for example a patient having a clinically diagnosed inflammatory disease of the digestive tract such as chronic gastritis or IBD, including UC and CD. Animal models in experimental investigations relevant to human disease are also examples of "subjects" herein, and can include for example rodents (e.g., mouse, rat, guinea pig), lagomorphs (e.g., rabbit), carnivores (e.g., cat, dog), or nonhuman primates (e.g., monkey, chimpanzee). Further, the subject can be an animal (for example a domestic, farm, working, sporting or zoo animal) in veterinary care.

The compound useful according to the present invention has two acid moieties that, under suitable conditions, can form salts with suitable bases, and an amino group that, under suitable conditions, can form salts with suitable acids. Internal salts can also be formed. The compound can be used in its free acid/base form or in the form of an internal salt, an acid addition salt or a salt with a base.

Acid addition salts can illustratively be formed with inorganic acids such as mineral acids, for example sulfuric acid, phosphoric acids or hydrohalic (e.g., hydrochloric or hydrobromic) acids; with organic carboxylic acids such as (a) $C_{1-4}$ alkanecarboxylic acids which may be unsubstituted or substituted (e.g., halosubstituted), for example acetic acid, (b) saturated or unsaturated dicarboxylic acids, for example oxalic, malonic, succinic, maleic, fumaric, phthalic or terephthalic acids, (c) hydroxycarboxylic acids, for example ascorbic, glycolic, lactic, malic, tartaric or citric acids, (d) amino acids, for example aspartic or glutamic acids, or (e) benzoic acid; or with organic sulfonic acids such as $C_{1-4}$ alkanesulfonic acids or arylsulfionic acids which may be unsubstituted (e.g., halosubstituted), for example methanesulfonic acid or p-toluenesulfonic acid.

Salts with bases include metal salts such as alkali metal or alkaline earth metal salts, for example sodium, potassium or magnesium salts; or salts with ammonia or an organic amine such as morpholine, thiomorpholine, piperidine, pyrrolidine, a mono-, di- or tri-lower alkyl amine, for example ethylamine, tert-butylamine, diethylamine, diisopropylamine, triethylamine, tributylamine or dimethylpropylamine, or a mono-, di- or tri-(hydroxy lower alkyl) amine, for example monoethanolamine, diethanolamine or triethanolamine.

Alternatively, a prodrug of the compound or a salt of such prodrug can be used. A prodrug is a compound, typically itself having weak or no pharmaceutical activity, that is cleaved, metabolized or otherwise converted in the body of a subject to an active compound, in this case GL1001. Examples of prodrugs are esters, particularly alkanoyl esters and more particularly $C_{1-6}$ alkanoyl esters. Other examples include carbamates, carbonates, ketals, acetals, phosphates, phosphonates, sulfates and sulfonates. Various prodrugs of GL1001, and methods of making such prodrugs, are disclosed, for instance, in above-referenced U.S. Pat. No. 6,632,830 and U.S. Published Patent Application No. 2004/0082496.

The compound should be administered in a therapeutically effective amount. What constitutes a therapeutically effective amount depends on a number of factors, including the particular subject's age and body weight, the nature, stage and severity of the disease, the particular effect sought (e.g., reduction of inflammation, alleviation of symptoms, maintenance of remission, etc.) and other factors, but for most subjects a dosage amount of about 0.5 to about 5000 mg/day, more typically about 5 to about 1000 mg/day, will be found suitable. In particular embodiments, the dosage employed is about 10 to about 800 mg/day, about 50 to about 750 mg/day or about 100 to about 600 mg/day; illustratively about 50, about 100, about 150, about 200, about 250, about 300, about 350, about 400, about 450, about 500, about 550, about 600, about 650, about 700 or about 750 mg/day.

Where a salt or prodrug of the compound is used, the amount administered should be an amount delivering a daily dosage of the compound as set forth above.

The above dosages are given on a per diem basis but should not be interpreted as necessarily being administered on a once daily frequency. Indeed the compound, or salt or prodrug thereof, can be administered at any suitable frequency, for example as determined conventionally by a physician taking into account a number of factors, but typically about four times a day, three times a day, twice a day, once a day, every second day, twice a week, once a week, twice a month or once a month. The compound, or salt or prodrug thereof, can alternatively be administered more or less continuously, for example by parenteral infusion in a hospital setting. In some situations a single dose may be administered, but more typically administration is according to a regimen involving repeated dosage over a treatment period. In such a regimen the daily dosage and/or frequency of administration can, if desired, be varied over the course of the treatment period, for example introducing the subject to the compound at a relatively low dose and then increasing the dose in one or more steps until a full dose is reached.

The treatment period is generally as long as is needed to achieve a desired outcome, for example induction or maintenance of remission, alleviation of symptoms, etc. In some situations it will be found useful to administer the drug intermittently, for example for treatment periods of days, weeks or months separated by non-treatment periods. Such intermittent administration can be timed, for example, to correspond to flares of the disease.

Administration can be by any suitable route, including without limitation oral, buccal, sublingual, intranasal, intraocular, rectal, vaginal, transdermal or parenteral (e.g., intradermal, subcutaneous, intramuscular, intravenous, intra-arterial, intratracheal, intraventricular, intraperitoneal, etc.) routes, and including by inhalation or implantation.

While it can be possible to administer the compound, or a salt or prodrug thereof unformulated as active pharmaceutical ingredient (API) alone, it will generally be found preferable to administer the API in a pharmaceutical composition that comprises the API and at least one pharmaceutically acceptable excipient. The excipient(s) collectively provide a vehicle or carrier for the API. Pharmaceutical compositions adapted for all possible routes of administration are well known in the art and can be prepared according to principles and procedures set forth in standard texts and handbooks such as those individually cited below.

USIP, ed. (2005) *Remington: The Science and Practice of Pharmacy,* 21st ed., Lippincott, Williams & Wilkins.

Allen et al. (2004) *Ansel's Pharmaceutical Dosage Forms and Drug Delivery Systems,* 8th ed., Lippincott, Williams & Wilkins.

Suitable excipients are described, for example, in Kibbe, ed. (2000) *Handbook of Pharmaceutical Excipients,* 3rd ed., American Pharmaceutical Association.

Examples of formulations that can be used as vehicles for delivery of the API in practice of the present invention include, without limitation, solutions, suspensions, powders, granules, tablets, capsules, pills, lozenges, chews, creams, ointments, gels, liposomal preparations, nanoparticulate preparations, injectable preparations, enemas, suppositories, inhalable powders, sprayable liquids, aerosols, patches, depots and implants.

Illustratively, in a liquid formulation suitable, for example, for parenteral, intranasal or oral delivery, the API can be present in solution or suspension, or in some other form of dispersion, in a liquid medium that comprises a diluent such as water. Additional excipients that can be present in such a formulation include a tonicifying agent, a buffer (e.g., a tris, phosphate, imidazole or bicarbonate buffer), a dispersing or suspending agent and/or a preservative. Such a formulation can contain micro- or nanoparticulates, micelles and/or liposomes. A parenteral formulation can be prepared in dry reconstitutable form, requiring addition of a liquid carrier such as water or saline prior to administration by injection.

For rectal delivery, the API can be present in dispersed form in a suitable liquid (e.g., as an enema), semi-solid (e.g., as a cream or ointment) or solid (e.g., as a suppository) medium. The medium can be hydrophilic or lipophilic.

For oral delivery, the API can be formulated in liquid or solid form, for example as a solid unit dosage form such as a tablet or capsule. Such a dosage form typically comprises as excipients one or more pharmaceutically acceptable diluents, binding agents, disintegrants, wetting agents and/or antifrictional agents (lubricants, anti-adherents and/or glidants). Many excipients have two or more functions in a pharmaceutical composition. Characterization herein of a particular excipient as having a certain function, e.g., diluent, binding agent, disintegrant, etc., should not be read as limiting to that function.

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 5% to about 99%, for example about 10% to about 85%, or about 20% to about 80%, by weight of the composition. The diluent or diluents selected preferably exhibit suitable flow properties and, where tablets are desired, compressibility.

Lactose, microcrystalline cellulose and starch, either individually or in combination, are particularly useful diluents.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like. One or more binding agents and/or adhesives, if present, typically constitute in total about 0.5% to about 25%, for example about 0.75% to about 15%, or about 1% to about 10%, by weight of the composition.

Povidone is a particularly useful binding agent for tablet formulations, and, if present, typically constitutes about 0.5% to about 15%, for example about 1% to about 10%, or about 2% to about 8%, by weight of the composition.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.2% to about 10%, or about 0.2% to about 5%, by weight of the composition.

Croscarmellose sodium and crospovidone, either individually or in combination, are particularly useful disintegrants for tablet or capsule formulations, and, if present, typically constitute in total about 0.2% to about 10%, for example about 0.5% to about 7%, or about 1% to about 5%, by weight of the composition.

Wetting agents, if present, are normally selected to maintain the drug or drugs in close association with water, a condition that is believed to improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like. One or more wetting agents, if present, typically constitute in total about 0.25% to about 15%, preferably about 0.4% to about 10%, and more preferably about 0.5% to about 5%, by weight of the composition.

Wetting agents that are anionic surfactants are particularly useful. Illustratively, sodium lauryl sulfate, if present, typically constitutes about 0.25% to about 7%, for example about 0.4% to about 4%, or about 0.5% to about 2%, by weight of the composition.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 8%, or about 0.2% to about 5%, by weight of the composition. Magnesium stearate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.1% to about 10%, for example about 0.1% to about 5%, or about 0.1% to about 2%, by weight of the composition.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.1% to about 10%, for example about 0.1% to about 5%, or about 0.1% to about 2%, by weight of the composition.

Talc and colloidal silicon dioxide, either individually or in combination, are particularly useful anti-adherents and glidants.

Other excipients such as buffering agents, stabilizers, antioxidants, antimicrobials, colorants, flavors and sweeteners are known in the pharmaceutical art and can be used. Tablets can be uncoated or can comprise a core that is coated, for example with a nonfunctional film or a release-modifying or enteric coating. Capsules can have hard or soft shells comprising, for example, gelatin and/or HPMC, optionally together with one or more plasticizers.

A pharmaceutical composition useful herein typically contains the compound or salt or prodrug thereof in an amount of about 1% to about 99%, more typically about 5% to about 90% or about 10% to about 60%, by weight of the composition. A unit dosage form such as a tablet or capsule can conveniently contain an amount of the compound providing a single dose, although where the dose required is large it may be necessary or desirable to administer a plurality of dosage forms as a single dose. Illustratively, a unit dosage form can comprise the compound in an amount of about 10 to about 800 mg, for example about 50 to about 750 mg or about 100 to about 600 mg; or, in particular illustrative instances, about 50, about 100, about 150, about 200, about 250, about 300, about 350, about 400, about 450, about 500, about 550, about 600, about 650, about 700 or about 750 mg.

In one embodiment of the invention, a method is provided for treating an inflammatory disease of the digestive tract, e.g., chronic gastritis or IBD, in a subject.

In another embodiment, a method is provided for reducing or alleviating inflammation or a pathological process associated therewith or secondary thereto in a subject having an inflammatory disease of the digestive tract, e.g., chronic gastritis or IBD.

In yet another embodiment, a method is provided for promoting healing of mucosal ulceration in a subject having an inflammatory disease of the digestive tract, e.g., chronic gastritis or IBD.

In yet another embodiment, a method is provided for inducing or maintaining remission of an inflammatory disease of the digestive tract, e.g., chronic gastritis or IBD, in a subject.

According to each of these embodiments, the method comprises administering to the subject a therapeutically effective amount of GL1001 or a pharmaceutically acceptable salt thereof or prodrug thereof.

Unless the context demands otherwise, the term "treat," "treating" or "treatment" herein includes preventive or prophylactic use of an agent, for example GL1001, in a subject at risk of, or having a prognosis including, an inflammatory disease of the digestive tract, as well as use of such an agent in a subject already experiencing such a disease, as a therapy to alleviate, relieve, reduce intensity of or eliminate one or more symptoms of the disease or an underlying cause thereof. Thus treatment includes (a) preventing a condition or disease from occurring in a subject that may be predisposed to the condition or disease but in whom the condition or disease has not yet been diagnosed; (b) inhibiting the condition or disease, including arresting its development; and/or (c) relieving, alleviating or ameliorating the condition or disease, or primary or secondary signs and symptoms thereof, including promoting, inducing or maintaining remission of the disease.

Figure 1:
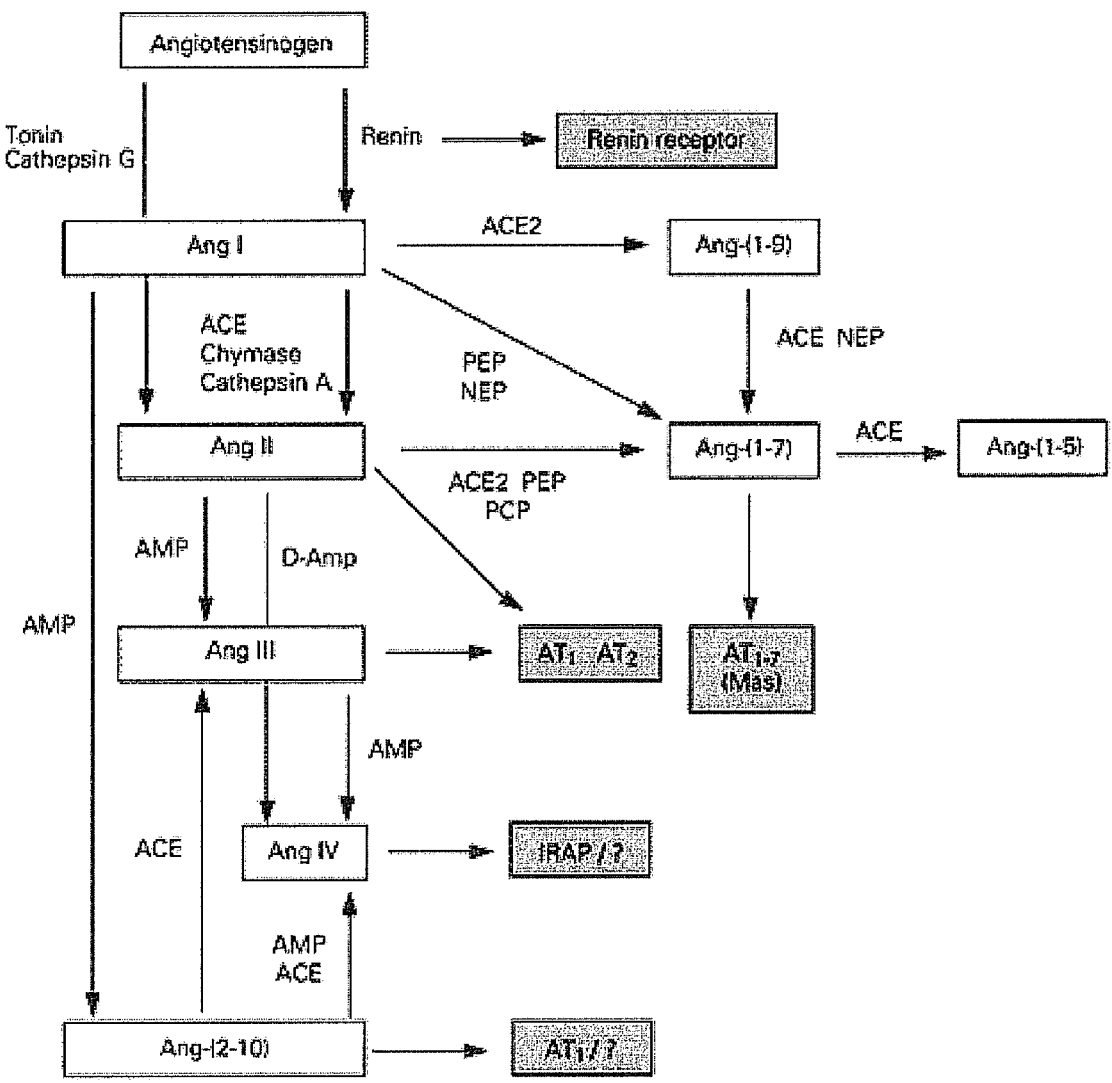
FIG. 1 is a schematic representation of enzymatic pathways of the renin-angiotensin system (RAS) involved in generation of angiotensin peptides. Key:
ACE=angiotensin converting enzyme;
AMP=aminopeptidase;
Ang=angiotensin;
AT$_1$=angiotensin II type 1 receptor;
AT$_{1-7}$=angiotensin (1-7) receptor;
AT$_2$=angiotensin II type 2 receptor;
D-Amp=dipeptidyl aminopeptidase;
IRAP=insulin regulated aminopeptidase;
NEP=neutral endopeptidase 24.11;
PCP=prolyl carboxypeptidase;
PEP=prolyl endopeptidase.

In accordance with methods of the invention, it has surprisingly been found that GL1001 inhibits TNFα induced activation of NF-κB in recombinant HeLa reporter cells. This finding is reported in greater detail in Example 2 below. GL1001 is a known ACE2 inhibitor, thus its effect on the renin-angiotensin system (RAS) might be predicted to involve increase in level of angiotensin II (see FIG. 1), which, as indicated above is implicated in a variety of pro-inflammatory effects. The present inventors have found, contrary to such prediction, that activation of NF-κB, a key mediator for synthesis of pro-inflammatory cytokines, is not promoted but inhibited by GL1001.

It has further surprisingly been found that GL1001 inhibits in vivo basal NF-κB dependent transcription in recombinant reporter mice. This finding is reported in greater detail in Example 3 below, and appears to further support an anti-inflammatory effect of GL1001 that is contrary to expectation based on its ACE2 inhibitory properties and present understanding of the role of ACE2 in the RAS.

It has still further surprisingly been found that in a mouse model for IBD (the dextran sodium sulfate (DSS) mouse model), administration of GL1001 delayed progression of the disease. This is strong evidence suggesting therapeutic effectiveness of GL1001 in human IBD.

It has still further surprisingly been found that ACE2 mRNA expression in tissues of the digestive tract is especially strongly elevated in chronic gastritis. It is accordingly contemplated that elevation of ACE2 in chronic gastritis is a potential pathogenic factor in that disease and that administration of an ACE2 inhibitor such as GL1001 is beneficial in treatment of chronic gastritis.

Description herein relating to actual or putative mechanisms of action of GL1001 is provided in the interest of full disclosure, but it is emphasized that the present invention is not bound by any theory as to mechanism of action.

In some embodiments, the subject has Crohn's disease (CD). The CD can be active or in remission. Degree of activity of CD can be quantified using any suitable score or index.

Various indices have been reviewed, for example, by Naber & de Jong (2003) *Neth. J. Med.* 61(4):105-110.

"Activity index" as used herein for Crohn's disease is defined as the Crohn's disease activity index (CDAI) developed by Best et al (1976) *Gastroenterology* 70(3):439-444. An activity index not less than about 220 is generally associated with active CD.

For a subject having active CD, GL1001 can be administered according to a regimen, including dose, frequency and treatment period, effective to achieve a clinically meaningful decrease in activity index. In various embodiments, a decrease of at least about 30 points, at least about 50 points, at least about 70 points or at least about 90 points in the activity index is obtained. The decrease, according to some embodiments, is sufficient to bring the activity index below about 220 or to achieve clinical remission of the CD.

The subject having CD can, in some embodiments, have fistulizing CD. In such a case, GL1001 can be administered according to a regimen, including dose, frequency and treatment period, effective for example to achieve a reduction in draining fistulas or to maintain fistula closure.

The subject having CD is, in some embodiments, a pediatric patient.

In some embodiments, the subject has ulcerative colitis (UC). The UC can be active or in remission. Degree of activity of UC can be quantified using any of the indices available for this disease, including the Mayo score as referenced by Naber & de Jong (2003), supra.

Methods of the present invention can be useful, for example, in subjects having moderately to severely active UC, typically exhibiting a Mayo score not less than about 6. For such a subject, GL1001 can be administered according to a regimen, including dose, frequency and treatment period, effective to achieve a clinically meaningful decrease in Mayo score. In various embodiments, a decrease of at least about 2 points, at least about 3 points, at least about 4 points or at least about 5 points; or a decrease of at least about 20%, at least about 30%, at least about 40% or at least about 50%, in Mayo score is obtained. In one embodiment, a decrease of at least about 30% and at least about 3 points is obtained. The decrease, according to some embodiments, is sufficient to bring Mayo score below about 6 or to achieve clinical remission of the UC.

The subject having UC can have any of the known variants or types of UC, including ulcerative proctitis, left-sided colitis, pancolitis and fulminant colitis. In patients with fulminant colitis, treatment according to the present methods can reduce risk of serious complications such as colon rupture and toxic megacolon.

Methods of the invention can also be useful in subjects having IBD (either CD or UC) that is in a period of inactivity or remission. For such subjects, GL1001 can be administered according to a regimen, including dose, frequency and treatment period, effective to achieve prolongation of the period of inactivity or remission.

In some embodiments, administration of GL1001 is associated with or results in alleviation of at least one sign or symptom of IBD. Examples of signs or symptoms that can be alleviated include, without limitation, diarrhea (which can be severe enough to result in dehydration and even shock), loose stools, abdominal pain (which can be moderate to severe and can be accompanied by nausea and/or vomiting), abdominal cramping, rectal pain, tenesmus, rectal bleeding, blood in feces (including occult blood in less severe cases), reduced appetite, weight loss, and combinations thereof. Secondary symptoms that can also be alleviated include fever, night sweats, fatigue and inflammation extending beyond the digestive tract, for example to the joints (arthritis) and/or skin.

In a more particular embodiment, at least one sign or symptom selected from diarrhea, rectal bleeding, weight loss and combinations thereof is alleviated.

In various embodiments, the subject has IBD (either CD or UC) that is, or has become, refractory to a baseline therapy comprising administration of a full dose of at least one baseline drug selected from the group consisting of aminosalicylates, corticosteroids, immunosuppressants, antibiotics and combinations thereof. The baseline therapy to which the subject is refractory can comprise a first line or second line therapy.

It is believed, without being bound by theory, that GL1001 has a mechanism of action on IBD that is different from that of the baseline drugs. In particular, GL1001, unlike such baseline drugs, is believed to inhibit ACE2. Usefulness of GL1001 in treatment of refractory IBD may to some degree reflect this different mechanism of action, but is not predicated thereon.

In a subject with refractory IBD, GL1001 can be administered in monotherapy or adjunctively with the baseline therapy or a portion thereof. In one embodiment, for example, GL1001 is, at least initially, administered adjunctively with the baseline therapy. In another embodiment, GL1001 is administered adjunctively with the at least one baseline drug, which is administered at less than a full dose. In yet another embodiment, GL1001 is administered adjunctively with the at least one baseline drug according to a regimen, including dose, frequency and treatment period, wherein, upon achieving clinical remission of the IBD, the at least one baseline drug is withdrawn. Withdrawal of the at least one baseline drug can be implemented all at once, but is more typically implemented over a period of time by tapered or stepwise dose reduction.

Withdrawal, for example by tapered dose reduction, is often especially desirable where the at least one baseline drug comprises a corticosteroid, because of adverse side effects that can accompany prolonged use of such a drug.

In another embodiment, GL1001 is administered to a subject having IBD that is, or has become, refractory to a first line therapy comprising an aminosalicylate, such administration being in place of a corticosteroid. There is thus provided a method for avoiding corticosteroid therapy in a subject having aminosalicylate-refractory IBD, comprising administering a therapeutically effective amount of GL1001, optionally in adjunctive therapy with an aminosalicylate, but in the absence of corticosteroids. Corticosteroid avoidance is of particular importance in subjects having a history of adverse reaction to corticosteroids or having risk factors that predispose them to such adverse reaction.

Whether or not the disease is refractory to other drugs, GL1001 can be administered in co-therapy with one or more additional agents, for example agents addressing signs, symptoms, underlying causes, contributory factors or secondary conditions associated with IBD.

The term "therapeutic combination" herein refers to a plurality of agents that, when administered to a subject together or separately, are co-active in bringing therapeutic benefit to the subject. Such administration is referred to as "combination therapy," "co-therapy," "adjunctive therapy" or "add-on therapy." For example, one agent can potentiate or enhance the therapeutic effect of another, or reduce an adverse side effect of another, or one or more agents can be effectively administered at a lower dose than when used alone, or can provide greater therapeutic benefit than when used alone, or can complementarily address different aspects, symptoms or etiological factors of a disease or condition.

For example, GL1001 can be administered in combination or adjunctive therapy with at least one additional agent selected from aminosalicylates, corticosteroids, immunosuppressants, anti-TNFα agents and combinations thereof.

Nonlimiting examples of aminosalicylates include balsalazide, mesalamine, olsalazine, sulfasalazine, pharmaceutically acceptable salts thereof and combinations thereof.

Nonlimiting examples of corticosteroids include beclomethazone, beclomethazone dipropionate, budesonide, dexamethasone, fluticasone, hydrocortisone, methylprednisolone, prednisone, prednisolone, prednisolone-21-methasulfobenzoate, tixocortol, pharmaceutically acceptable salts thereof and combinations thereof.

Nonlimiting examples of immunosuppressants include azathioprine, cyclosporin (e.g., cyclosporin A), mercaptopurine, methotrexate, tacrolimus, pharmaceutically acceptable salts thereof and combinations thereof.

In one embodiment, GL1001 is administered in combination or adjunctive therapy with an anti-TNFα agent such as infliximab.

The two or more active agents administered in combination or adjunctive therapy can be formulated in one pharmaceutical preparation (single dosage form) for administration to the subject at the same time, or in two or more distinct preparations (separate dosage forms) for administration to the subject at the same or different times, e.g., sequentially. The two distinct preparations can be formulated for administration by the same route or by different routes.

Separate dosage forms can optionally be co-packaged, for example in a single container or in a plurality of containers within a single outer package, or co-presented in separate packaging ("common presentation"). As an example of co-packaging or common presentation, a kit is contemplated comprising, in a first container, GL1001 or a pharmaceutically acceptable salt thereof or a prodrug thereof, and, in a second container, an additional agent such as any of those mentioned above. In another example, GL1001 or a pharmaceutically acceptable salt thereof or a prodrug thereof and the additional agent are separately packaged and available for sale independently of one another, but are co-marketed or co-promoted for use according to the invention. The separate dosage forms may also be presented to a subject separately and independently, for use according to the invention.

Depending on the dosage forms, which may be identical or different, e.g., fast release dosage forms, controlled release dosage forms or depot forms, the GL1001 and the additional agent may be administered on the same or on different schedules, for example on a daily, weekly or monthly basis.

In one embodiment, the invention provides a therapeutic combination comprising (a) GL1001 or a pharmaceutically acceptable salt thereof or prodrug thereof, and (b) at least one additional agent selected from aminosalicylates, corticosteroids, immunosuppressants, anti-TNFα agents and combinations thereof. Specific examples of such additional agents are illustratively as listed above.

EXAMPLES

Example 1

ACE2 mRNA Expression in Normal and Disease States

Donoghue et al. (2000), supra, reported finding ACE2 transcripts mainly in heart, kidney and testis, out of 23 normal human tissues examined, and ACE2 protein (via immunohistochemistry) predominantly in the endothelium of coronary and intrarenal vessels and in renal tubular epithelium.

Further, Tipnis et al. (2000) *J. Biol. Chem.* 275(43):33238-33243 reported Northern blotting analyses showing that the ACE2 mRNA transcript is most highly expressed in testis, kidney and heart.

Komatsu et al. (2002) *DNA Seq.* 13:217-220 reported molecular cloning of mouse angiotensin-converting enzyme-related carboxypeptidase (mACE2) showing 83% identity with human ACE2, and Northern blot analysis showing transcripts were expressed mainly in kidney and lungs.

More recently, Gembardt et al. (2005) *Peptides* 26:1270-1277 analyzed ACE2 mRNA and protein expression in various normal tissues of mice and rats, reporting at least detectable levels of ACE2 mRNA in all tested organs of both species (ventricle, kidney, lung, liver, testis, gallbladder, forebrain, spleen, thymus, stomach, ileum, colon, brainstem, atrium, and adipose tissue). In both species ileum tissue showed the highest expression of ACE2 mRNA, with the mouse exceeding the rat in ACE2 mRNA expression in this organ and also in the kidney and colon.

Burrel et al. (2005) *Eur. Heart J.* 26:369-375 recently reported that myocardial infarction increases ACE2 expression in rat and human heart.

ACE2 mRNA expression has now been examined in various human tissues from normal and diseased subjects, using the BioExpress® System of Gene Logic Inc. This system includes mRNA expression data from about 18,000 samples, of which about 90% are from human tissues, comprising both normal and diseased samples from about 435 disease states. In brief, human tissue samples, either from surgical biopsy or post-mortem removal, were processed for mRNA expression profile analysis using Affymetrix GeneChips®. Each tissue sample was examined by a board-certified pathologist to confirm pathological diagnoses. RNA isolation, cDNA synthesis, cRNA amplification and labeling, hybridizations, and signal normalization were carried out using standard Affymetrix protocols. Computational analysis was performed using Genesis Enterprise System® Software and the Ascenta® software system (Gene Logic Inc).

In agreement with Donoghue et al. (2000), supra, and Tipnis et al. (2000), supra, the present study showed relatively high levels of ACE2 transcripts in normal human heart, kidney and testis (data not shown). However, excluding those three normal tissues, the top 8 highest expression levels of ACE2 mRNA in 70 additional normal human tissues that were examined are listed in Table 1 below, in descending order of mean expression level (given as the "average relative level," i.e., sample set signal level in arbitrary units, normalized to the lowest signal level in all tested samples, averaged for two different probe fragments).

These top 8 normal tissues in Table 1 (and heart, kidney and testis as well) showed average relative levels of ACE2 mRNA expression greater than 4.0, while the remaining 62 normal tissues examined showed average relative levels less than 4.0.

Table 1 also shows that four of the top five highest expression levels of ACE2 mRNA in normal human tissues (other than heart, kidney and testis) were in components of the gastrointestinal tract, namely (in descending order of expression level): duodenum, small intestine, colon and stomach.

TABLE 1

Relative levels of ACE2 mRNA expression in normal tissues

| Sample Set | Average Relative Level |
|---|---|
| Duodenum | 221.2 |
| Small Intestine | 167.9 |
| Gallbladder | 109.9 |
| Colon | 13.6 |
| Stomach | 10.1 |
| Ovary | 5.7 |
| Pancreas | 4.3 |
| Liver | 4.2 |

Examination of ACE2 mRNA expression in disease states encompassed by the BioExpress® System showed elevation of ACE2 mRNA in only a few conditions, mainly inflammatory conditions of components of the gastrointestinal tract. Thus, Table 2 shows that ACE2 mRNA expression was elevated (in descending order of average fold change vs. normal) in inflammatory conditions of the stomach (chronic gastritis), major salivary gland (excluding parotid) (chronic sialadenitis), and colon (Crohn's disease, active (chronic or acute inflammation)). In contrast, the levels of ACE2 mRNA in colon with active ulcerative colitis (chronic or acute inflammation), and in small intestine with active Crohn's disease (chronic or acute inflammation), were substantially unchanged from the already significant levels in corresponding normal tissues shown in Table 1.

TABLE 2

Effects of inflammatory conditions on ACE2 mRNA expression in digestive tract tissues

| Sample Set | Average Fold Change vs. Normal |
|---|---|
| Stomach, Chronic Gastritis | 8.2 |
| Major Salivary Gland (Excluding Parotid), Chronic Sialadenitis | 7.5 |
| Colon, Crohn's Disease, Active (Chronic Inflammation) | 2.2 |
| Colon, Crohn's Disease, Active (Acute Inflammation) | 1.7 |
| Colon, Ulcerative Colitis, Active (Chronic Inflammation) | 0.9 |
| Colon, Ulcerative Colitis, Active (Acute Inflammation) | 1.0 |
| Small Intestine, Crohn's Disease, Active (Chronic Inflammation) | 0.4 |
| Small Intestine, Crohn's Disease, Active (Acute Inflammation) | 0.8 |

The above findings taken together show that 4 of the top 11 highest expression levels of ACE2 mRNA found in normal human tissues are in components of the digestive tract, and that the majority of examined disease conditions that involve elevated ACE2 mRNA expression are inflammatory conditions of the digestive tract. Accordingly, these findings suggest that high levels of ACE2 mRNA expression could be a pathogenic factor and, hence, reduction of ACE2 activity could provide therapeutic benefit, in at least some inflammatory conditions of the digestive tract, particularly in the stomach (chronic gastritis), major salivary gland (chronic sialadenitis), and colon (Crohn's disease with chronic or acute inflammation). Further, although ACE2 mRNA levels were not elevated in colon with ulcerative colitis or small intestine with Crohn's disease, the already substantial levels of such mRNA in normal colon and small intestine suggest at least that ACE2 activity is present and, therefore, could still constitute a pathogenic factor in these two diseased tissues.

Example 2

Inhibition by GL1001 of TNFα-Induced Activation of NF-κB in Recombinant HeLa Reporter Cells Both in human IBD and in murine models of IBD, inflammation is likely to depend, at least in part, on activation and nuclear translocation of NF-κB family members. See, e.g., Fichtner-Feigl et al. (2005) *J. Clin. Invest.* 115:3057-3071 and sources cited therein. Thus, in Th1-mediated inflammations dependent on IL-12 and/or IL-23, synthesis of these cytokines is regulated by NF-κB transcription factors. In Th2-mediated inflammations dependent on IL-4 or IL-13, synthesis of these cytokines is also dependent on NF-κB transcription factors, albeit more indirectly than that of IL-12 and IL-23. Thus one method of treating the inflammation of IBD can be to administer agents that inhibit NF-κB activity, and indeed Fichtner-Feigl et al. (2005), supra, have shown that NF-κB decoy oligodeoxynucleotides (ODNs) that prevent NF-κB activation of gene expression are effective in treating and preventing various models of Th1- and Th2-mediated IBD in mice, including acute trinitrobenzene sulfonic acid (TNBS) induced colitis, as assessed by clinical course and effect on Th1 cytokine production; chronic TNBS induced colitis, inhibiting both production of IL-23/IL-17 and development of fibrosis; and oxazolone induced colitis, a Th2-mediated inflammatory process.

To test the ACE2 inhibitor GL1001 for anti-inflammatory activity relevant to IBD, effects of the compound on activation of NF-κB dependent transcription by TNFα were examined in recombinant reporter cells containing a construct with a luciferase reporter gene under control of NF-κB dependent regulatory sequences, thereby allowing detection of NF-κB dependent transcription by measuring reporter enzyme using a conventional luciferase activity assay based on detection of generated light.

In particular, HeLa cells (American Type Culture Collection) were grown in Dulbecco's modified Eagles medium (DMEM) supplemented with 10% fetal calf serum and transiently transfected with an NF-κB-luc construct (Stratagene, Inc.), as follows (with all incubation steps at 37 C unless otherwise indicated). Cells were seeded and grown to about 70% confluency in a 10 cm cell culture dish. Plasmid DNA (10 μg) was added to 1 ml serum free DMEM media in a tube. Fugene 6 transfection reagent (30 μl) (Roche) was then pipetted slowly into the tube and the contents were gently mixed by inversion. The mixture was incubated at room temperature for 15 minutes and then added dropwise to cells in one 10 cm dish. Following incubation for 24 hours, cells were detached from the plate with Trypsin-EDTA (Gibco-BRL), transferred to wells in a clear-bottom white 96-well test plate (Fisher) with 100 μl per well serum free DMEM, at a density of $3 \times 10^4$ cells per well, and allowed to attach overnight. Compound (GL1001) was then added to wells at a concentration of approximately 0, 0.008, 0.04, 0.2, 1.0 or 5.0 μM, followed immediately by addition of TNFα (R&D) to a final concentration of 20 ng/ml. After incubation for 6 hours, 100 μl of Bright-Glo Luciferase buffer (Promega, Cat# E2610) was added, and the plate was incubated at room temperature, with mild shaking, for 10 min. Bioluminescence was then measured using a Veritas luminometer (Turner BioSystems). Each plotted data point represents the average bioluminescence of 4 independent wells.

As shown in FIG. 2, GL1001 significantly inhibited TNFα induced activation of NF-κB dependent transcription at all tested concentrations, with over 80% inhibition at 8 nM and maximal inhibition over 95% at 0.2 μM. These results indicate that the ACE2 inhibitor GL1001 has potent anti-inflammatory activity, namely inhibition of activation of the NF-κB signaling pathway by the inflammatory cytokine TNFα, that is relevant to IBD. The present inventors are not aware of any previous report of such anti-inflammatory activity for any ACE2 inhibitor.

Example 3

Inhibition by GL1001 of In Vivo Basal NF-κB Dependent Transcription in Recombinant Reporter Mice GL1001 was further tested for in vivo anti-inflammatory activity by examining its effects on basal levels of NF-κB dependent transcription in mice engineered in the germline with a construct containing an NF-κB enhancer linked to a luciferase gene (i.e., NF-κB:Luc mice), such that this NF-κB reporter construct is present in all cells of the mice.

More particularly, transgenic NF-κB:Luc mice were generated using three NF-κB response elements from the Igκ light chain promoter fused to a firefly luciferase gene as described by Carlsen et al. (2002) $J.$ $Immunol.$ 168:1441-1446. Pronuclear microinjection of purified construct DNA was used to generate transgenic founders in the C57BL/6 XCBA/J background. Founders were subsequently back crossed to the C57BL/6 albino background. All experimental protocols were approved by the Institutional Animal Care and Use Committee and conform to the ILAR guide for the care and used of laboratory animals. For in vivo imaging, NF-κB:Luc mice were injected intraperitoneally with luciferin (150 mg/kg) 10 minutes before imaging, anesthetized (using 1-3% isoflurane) and placed into a light-tight camera box. Mice were imaged for up to two minutes from the dorsal or ventral aspects at high-resolution settings with a field of view of 20 cm. The light emitted from the transgene was detected by an IVIS® Imaging System 200 Series (Xenogen Corporation, Alameda, Calif.), digitized and displayed on a monitor. The Living Image® software (Xenogen Corporation, Alameda, Calif.; see Rice et al. (2002) $J.$ $Biomed.$ $Opt.$ 6:432-440) displays data from the camera using a pseudocolor scale with colors representing variations of signal intensity. Signal data were also quantitated and archived using the Living Image® software. Photons of light were quantitated using an oval region of interest (ROI) of varying sizes depending on the procedure, as described further below.

For luciferase assays, organs were extracted and snap frozen in liquid nitrogen. All tissue samples were placed in lysis buffer with inhibitors (Passive Lysis Buffer (Promega) and Complete Mini Protease Inhibitor Cocktail (Roche, Indianapolis, Ind.)), and were homogenized using a tissue homogenizer (Handishear, Hand-held homogenizer, VirTis, Gardiner, N.Y.). Tissue homogenates were centrifuged and clarified lysates were used for luminometer assays and western blots. For the luminometer assays, Luciferase Assay Substrate (Luciferase Assay System, Promega) was prepared as indicated by the manufacturer and placed in disposable cuvettes. Tissue homogenates (20 μl) and substrate (100 μl) were mixed and measurements were taken in a Veritas Microplate Luminometer (Turner Designs, Sunnyvale, Calif.) with the parameters of a 2 second delay, 10-second. Background luminescence readings were obtained and the background readings were subtracted from the luminescent data. Protein concentrations were determined using the BCA Protein Assay Kit (Pierce, Rockford, Ill.) following the manufacturer's protocols and analyzed using a VERSAmax tunable microplate reader and associated Softmax Pro version 3.1.2 software (Molecular Devices, Sunnyvale Calif.). The luminescence for each of the protein lysates was calculated as arbitrary units of light per microgram of protein. Statistical analyses include MEAN, SEM and ANOVA and students t-test between treatment groups.

To test for in vivo effects of GL1001 on basal levels of NF-κB dependent transcription, male NF-κB:Luc mice were subjected to quantitative in vivo imaging of the abdominal area (using a fixed ROI of 2.76×3.7 cm) as described above, immediately before, and at 2, 4 and 6 hours after subcutaneous administration of 0, 3, 30 or 100 mg/kg GL1001 in saline. Whole body imaging showed that GL1001 significantly inhibited basal in vivo levels of NF-κB dependent transcription of the luciferase reporter gene, primarily in the abdominal region. As shown by the quantitative imaging data in FIG. 3, at 4 hours post LPS administration GL1001 significantly inhibited basal in vivo levels of NF-κB dependent transcription in the selected abdominal ROI by over 40% at 300 mg/kg (p<0.01 by ANOVA and Student's t-test), and to lesser but still significant extents at both lower doses.

In contrast to the results observed in NF-κB:Luc mice, no significant effect of GL1001 was observed on basal in vivo levels of reporter luciferase expression in AP-1:Luc mice constructed similarly to the present NF-κB:Luc mice (data not shown), in which reporter transcription was driven by an enhancer element responsive to activator protein-1 (AP-1), a known protooncogene thought to be involved in cell proliferation and tumor promotion.

Example 4

GL1001 Inhibits In Vivo LPS-Induced NF-κB Dependent Transcription in Recombinant Reporter Mice Bacterial lipopolysaccharide (LPS), a major component of the cell wall of gram-negative bacteria, is a highly biologically active molecule which stimulates macrophages to produce and release TNFα. See, e.g., Jersmann et al. (2001) $Infection$ $and$ $Immunity$ 69(3):1273-1279, and sources cited therein. One of the recognized associations of bacterial infection with cardiovascular events is the activation of endothelium and upregulation of adhesion molecules. The two major proinflammatory mediators implicated in the causation of cardiovascular events, bacterial LPS and TNFα have been found to cooperate to enhance the adhesive properties of endothelial cells by synergistically increasing expression of human endothelial adhesion molecules through activation of NF-κB and p38 mitogen-activated protein kinase signaling pathways.

GL1001 was further tested for in vivo anti-inflammatory activity by examining its effects on bacterial LPS induced NF-κB dependent transcription, in NF-κB:Luc mice. In particular, inflammation was induced in these mice at 6-10 weeks of age by administration of 0.5 mg/kg (i.v.) soluble LPS (sLPS; Sigma) one hour after administration of GL1001. Mice were subjected to quantitative abdominal imaging at 2, 4 and 6 h following LPS administration, as described above. In confirmatory experiments, and at the time point with the greatest modulation of luciferase signal, animals were euthanized and tissues were collected and preserved for further analysis. Luciferase signal was quantitated from several regions of interest. Statistical analyses include MEAN, SEM and ANOVA and student t-test between treatment groups.

Whole body imaging showed that GL1001 significantly inhibited LPS-induced in vivo levels of NF-κB-dependent transcription of the luciferase reporter gene, again primarily in the abdominal region. As shown by the quantitative imaging data in FIG. 4, LPS induced a strong NF-κB-dependent luciferase signal in control mice, indicating a strong NF-κB signaling response, as expected. In contrast, mice that were pretreated with GL1001 showed a significantly reduced LPS induced NF-κB signaling response, which could be measured quantitatively in the abdominal region. As inhibition of NF-κB-dependent luciferase activity was observed over the entire dose range of GL1001 in this experiment (30 mg/kg, 100 mg/kg, 300 mg/kg), the experiment was repeated using a slightly lower dose range (3-100 mg/kg). As shown in FIG. 5, in this lower dose range, GL1001 significantly reduced LPS induced NF-κB signaling at 30 and 100 mg/kg. These results show that systemic (subcutaneous) administration of the ACE2 inhibitor GL1001 showed significant in vivo anti-inflammatory activity, predominantly in the abdominal region, against bacterial LPS induced NF-κB dependent transcription as well as against basal NF-κB dependent transcription.

Examination of selected organs extracted from NF-κB:Luc mice treated with 0.5 mg/kg LPS and GL1001 at 30 mg/1 g or with 0.5 mg/kg LPS alone (FIG. 6) showed a significant (about 37-fold) reduction of LPS induced NF-κB-dependent transcription in stomachs of GL1001 treated mice, compared to mice treated with LPS alone, but no statistically significant decrease in LPS induced NF-κB signaling in pancreas and uterus, or in any other organ or organ part that was analyzed (data not shown), namely, liver, kidney, spleen, small intestine, large intestine (colon), mesenteric lymph nodes, cecum (first part of the colon after the small intestine), ovary, uterus, submandibular lymph nodes, brain, heart and lung.

GL1001 inhibition of LPS induced NF-κB activity in the mouse stomach is consistent with the present observation (above) of ACE2 mRNA expression in normal stomach tissue of human subjects, and with the report of ACE2 mRNA expression in the mouse stomach by Gembardt et al. (2005), supra. The fact that no inhibition of LPS induced NF-κB activity was observed in other murine tissues previously reported to express high levels of ACE2 mRNA (e.g., kidney, small intestine or colon; see Gembardt et al. (2005), supra) shows that the inhibitory effect on LPS induced NF-κB signaling predominantly in the abdominal region following systemic (subcutaneous) administration of GL1001 is primarily due to some activity of this ACE2 inhibitor in the stomach.

Example 5

GL1001 Inhibits IBD Induced in Mice by Dextran Sodium Sulfate (DSS)

GL1001 was further tested for in vivo anti-inflammatory activity by examining its effects on dextran sulfate sodium (DSS) induced colitis in mice. This IBD model shows reproducible morphological changes, which are very similar to those seen in patients with ulcerative colitis. See, e.g., Hollenbach et al. (2004) FASEB J. 18(13):1550-1552. See also Bryne et al (2006), Current Opinion in Drug Discovery & Development 8(2):207-217 and sources cited therein. These pathologies include predominant left-sided colonic inflammation, prominent regeneration of the colonic mucosa cells with dysplasia leading to colon cancer, shortening of the large intestine, focal crypt damage, and frequent lymphoid hyperplasia in both biological systems. Further, according to Hollenbach et al. (2004), supra, DSS-induced colitis in mice has a high value in assessing the efficacy of therapeutic agents commonly used in the treatment of colitis, since all therapeutically beneficial substances in human IBD were also shown to reduce the disease activity in this mouse model.

The study was designed with three groups: control (5 mice), 2.5% DSS alone (10 mice), and 2.5% DSS with GL1001 treatment (100 mg/kg subcutaneously per day) (10 mice). NF-κB:Luc mice were used to measure NF-κB activation as an indicator of inflammatory activity, as described above. In particular, organ specific luciferase activity was measured, in addition to body weight, fluid intake, occult fecal blood, organ weights and neutrophil infiltration (MPO assay). NF-κB:luc BL/6 albino background mice of 6-8 weeks of age were provided with 2.5% dextran sodium sulfate (DSS, MW 40,000; MP Biomedicals) in the drinking water. Mice were weighed, imaged and dosed with GL1001 daily. Fecal samples were collected from the bottom of the cages for each treatment group and tested for fecal consistency and occult blood using Hemocult Tape as directed by the manufacturer (Fisher Scientific) and fluid consumption was measured. At the conclusion of the study, the GI tract was removed, the various sections were cleaned and weighed, tissue samples were prepared for bioluminescent assays and myeloperoxidase (Myeloperoxidase assay kit, Cytostore) to look at neutrophil infiltration.

The mice were weighed and imaged at the time of daily GL1001 or vehicle control administration. Biophotonic images of the mice were acquired each day, as described above, with quantitative abdominal imaging results shown in FIG. 7. In this experiment there was an initial decrease in NF-κB-driven luciferase expression in both groups receiving DSS treatment, with a non-statistically significant divergence in luciferase expression that was maintained between the DSS only and DSS+100 mg/kg GL1001 groups throughout the experiment starting on study day 6. Water consumption was monitored for all of the animals and similar consumption rates indicate that DSS treated mice were all receiving similar amounts of DSS (FIG. 8).

Inflammatory bowel disease progression was monitored using an inflammatory bowel disease activity index which consists of the sum of percent weight loss, stool consistency and occult fecal blood divided by 3. Table 3 shows the ranking system for each of the measured parameters.

TABLE 3

Inflammatory bowel disease activity index scoring system

| Score | Weight loss (%) | Stool consistency | Blood in feces |
|-------|-----------------|-------------------|----------------|
| 0 | 0 or Gain | Normal | Negative |
| 1 | 1-4.9 | Soft | +/− |
| 2 | 5.0-9.9 | Mixed (Soft and Diarrhea) | + |
| 3 | 10-15 | Diarrhea | ++ |
| 4 | >15 | Bloody Diarrhea | Gross Blood |

A slight delay in disease activity was seen in the GL1001 group between days 3 and 8 of the study as shown as the results for the inflammatory bowel disease activity index which are plotted in FIG. 9. The reduction in body weight was significantly delayed between days 4 and 9 in the group receiving GL1001 as compared to the DSS only treatment group (FIG. 10).

At the conclusion of the study selected organs of the gastrointestinal tract were removed, cleaned and weighed, and the ratio of organ weight to final body weight was determined. As shown in FIG. 11, significant DSS induced organ weight increases were observed, and were completely prevented by GL1001, in both the cecum and large intestine (colon), but not in the stomach or small intestine.

In addition, sections of the gastrointestinal tract, as well as liver and kidney as controls, were homogenized and luciferase expression was recorded as units of light per µg protein, in FIG. 12. Organs showing an increase in luciferase expression were the cecum and large intestine in the DSS only group. The GL1001 treated group showed luciferase expression levels similar to those in the control group that received water only.

In summary, the ACE2 inhibitor GL1001 was shown to exhibit in vivo anti-inflammatory activity in dextran sulfate sodium (DSS) induced colitis in mice, since all assays of disease-related parameters showed either significant differences or corresponding trends between the DSS and DSS+GL1001 treatment groups. The facts that systemic (subcutaneous) administration of GL1001 reduced organ weights and DSS induced NF-κB signaling in the cecum and remainder of the large intestine (colon) show that this ACE2 inhibitor has anti-inflammatory activity in portions of the gastrointestinal tract relevant to both forms of human IBD, i.e., UC and CD, in addition to such activity against basal and LPS induced NF-κB signaling in the stomach.

In addition, GL1001 significantly delayed disease progression in the first week of this study, as shown by reductions in inflammatory bowel disease activity index, for instance. This activity index represents a composite assessment of three IBD symptoms, namely, weight loss, stool consistency (i.e., diarrhea), and blood in feces (i.e., bloody stools). As noted hereinabove, patients with UC most commonly present with bloody diarrhea, and weight loss also occurs in more severe cases. Similarly, patients with CD generally have ongoing diarrhea and weight loss, and may also have bloody stools.

Accordingly, the present study shows that GL1001 effectively treats common symptoms of human IBD in an animal model that reportedly has high value in assessing the efficacy of therapeutic agents commonly used in the treatment of colitis, since all therapeutically beneficial substances in human IBD were also shown to reduce the disease activity in this mouse model. See, e.g., Hollenbach et al. (2004), supra.

In a subsequent study in NF-κB:Luc mice, 2.5% DSS treatment tended to increase NF-κB signaling, as measured by luciferase expression, in distal colon and mesenteric lymph tissues, although these increases were generally not statistically significant. GL1001 at 300 mg/kg/day, administered twice daily by oral gavage, did not lower DSS-induced NF-κB signaling in this study. Reasons for lack of effect of GL1001 in this study are not fully understood at present.

Example 6

GL1001 Reduces DSS-Induced Histological Effects in Colon of Balb/c Mice

A study was designed with five groups of Balb/c mice: naïve control, DSS followed by vehicle, DSS followed by dexamethasone 3 mg/kg/day, DSS followed by GL1001 10 mg/kg/day, and DSS followed by GL1001 100 mg/kg/day. Administration of DSS was via drinking water (DSS 5% in water), from day 0 to day 7 of the study. Thereafter, drinking water did not include DSS. Administration of vehicle, dexamethasone and GL1001 was subcutaneous, once daily, from day 7 until termination of the study (day 14).

At termination of the study, samples from proximal, transverse and distal portions of the colon of each animal were collected for histological analysis, which included:

(a) inflammation score (0-5), based on leukocyte infiltration in mucosa and submucosa, crypt abscess and edema;
(b) glandular score (0-5), based on crypt destruction (crypts function to produce mucin and generate epithelium); and
(c) erosion score (0-5), based on integrity of epithelium or degree of ulceration thereof.

A total histopathological score was obtained by adding the scores from (a), (b) and (c) above.

No significant improvement in disease activity (based on fecal samples) was observed in this study from either dexamethasone or GL1001 treatment. However, as shown in FIG. 13, GL1001 at 100 mg/kg/day significantly reduced inflammation, glandular, erosion and total histopathological scores in distal colon samples. No significant histological effect was seen with dexamethasone or with GL1001 at 10 mg/kg/day.

Histological effect (reduction in inflammation and gland loss, and absence of erosion) of GL1001 in distal colon sections is clearly seen in FIG. 14, which presents comparative micrographs (50×) of histology sections taken from the distal section of the colon. In these micrographs M indicates more severely affected mucosa and E indicates edema.

The upper micrograph in FIG. 14 is from an animal treated with DSS followed by once-daily subcutaneous administration of vehicle. Severe inflammation, gland loss and erosion are seen.

The lower micrograph in FIG. 14 is from an animal treated with DSS followed by once-daily subcutaneous administration of GL1001 at 100 mg/kg. Inflammation and gland loss are mild, and no erosion is seen. The arrow indicates less severely affected mucosa.

Example 7

GL1001 Inhibits DSS-Induced Colitis in Balb/c Mice

A study was designed with six groups of Balb/c mice: naïve control, DSS followed by vehicle, DSS followed by GL1001 30 mg/kg/day, DSS followed by GL1001 100 mg/kg/day, DSS followed by GL1001 300 mg/kg/day, and DSS followed by sulfasalazine 150 mg/kg/day. Administration of DSS was via drinking water, from day 1 to day 6 of the study. Thereafter, drinking water did not include DSS. Administration of vehicle, GL1001 and sulfasalazine was subcutaneous, twice daily, from day 6 until termination of the study (day 16).

Body weight of each animal was measured at days 1, 3 and 5 (pre-initiation of GL1001 or sulfasalazine treatment) and at days 7, 9, 11 and 13 (post-initiation of GL1001 or sulfasalazine treatment). On these same days, disease activity measurements were recorded, including:

(a) rectal prolapse (0=no prolapse, 1=partial prolapse, 2=moderate prolapse, 3=full prolapse);
(b) stool consistency (0=solid pellet, 1=semi-solid, 2=soft stool, 3=diarrhea); and
(c) fecal occult blood (0=no blood present, 1=occult blood, 2=gross blood).

At termination of the study, colon length was determined and histological analysis was conducted as in Example 6.

Improvements in body weight, disease activity, colon length and histopathology were obtained with GL1001, at least at the 300 mg/kg/day dose. In general, these improvements were comparable to, in some cases apparently greater, than obtained with sulfasalazine treatment.

Body weight loss during and following DSS administration reached a maximum at day 9. Effects of various treatments on body weight loss at day 9 (as percentage of weight at day 5) are shown in FIG. 15.

Rectal prolapse score reached a maximum at day 9. Effects of various treatments on rectal prolapse at day 9 are shown in FIG. 16. Stool consistency and fecal occult blood scores reached a maximum at day 7. Effects of various treatments on stool consistency and fecal occult blood at day 7 are shown in FIGS. 17 and 18 respectively.

Effects of various treatments on colon length are shown in FIG. 19. Effects of various treatments on inflammation, crypt (glandular), erosion and total histopathological scores are shown in FIGS. 20, 21, 22 and 23 respectively.

All patents and publications cited herein are incorporated by reference into this application in their entirety.

The words "comprise", "comprises", and "comprising" are to be interpreted inclusively rather than exclusively.

What is claimed is:

1. A method for treating an inflammatory disease of the digestive tract in a subject experiencing such a disease, comprising administering to the subject a therapeutically effective amount of a compound selected from the group consisting of (S,S)-2-[1-carboxy-2- [3- (3,5-dichlorobenzyl)-3H-imidazol-4-yl]-ethylamino]-4-methyl- pentanoic acid and pharmaceutically acceptable salts thereof.

2. The method of claim 1, wherein the disease is chronic gastritis.

3. The method of claim 1, wherein the disease is inflammatory bowel disease.

4. The method of claim 3, wherein the inflammatory bowel disease is ulcerative colitis.

5. The method of claim 4, wherein the ulcerative colitis is moderately to severely active and exhibits a Mayo score not less than about 6.

6. The method of claim 3, wherein the inflammatory bowel disease is Crohn' s disease.

7. The method of claim 6, wherein the Crohn's disease is active and exhibits an activity index not less than about 220.

8. The method of claim 7, wherein the compound is administered according to a regimen effective to achieve clinical remission of the Crohn' s disease.

9. The method of claim 6, wherein the Crohn's disease is fistulizing Crohn's disease.

10. The method of claim 6, wherein the subject is a pediatric patient.

11. The method of claim 3, wherein the inflammatory bowel disease is in a period of inactivity or remission.

12. The method of claim 3, wherein the inflammatory bowel disease is refractory to a baseline therapy comprising administration of a full dose of at least one baseline drug selected from the group consisting of aminosalicylates, corticosteroids, immunosuppressants, antibiotics and combinations thereof.

13. The method of claim 12, wherein, at least initially, the compound is administered adjunctively with said baseline therapy.

14. The method of claim 12, wherein, at least initially, the compound is administered adjunctively with the at least one baseline drug, which is administered at less than a full dose.

15. The method of claim 12, wherein the compound is administered adjunctively with the at least one baseline drug therapy according to a regimen wherein, upon achieving clinical remission of the inflammatory bowel disease, the at least one baseline drug is withdrawn.

16. The method of claim 15, wherein withdrawal of the at least one baseline drug is implemented by tapered dose reduction.

17. The method of claim 15, wherein the at least one baseline drug comprises a corticosteroid.

18. The method of claim 3, further comprising administering to the subject at least one additional agent selected from the group consisting of aminosalicylates, corticosteroids, immunosuppressants, anti-TNFα agents and combinations thereof.

19. The method of claim 1, wherein the compound is administered in a dosage amount of about 0.5 to about 5000 mg/day.

* * * * *

UNITED STATES PATENT AND TRADEMARK OFFICE
CERTIFICATE OF CORRECTION

| | |
|---|---|
| PATENT NO. | : 7,842,709 B2 |
| APPLICATION NO. | : 11/851669 |
| DATED | : November 30, 2010 |
| INVENTOR(S) | : Louis Anthony Tartaglia et al. |

Page 1 of 1

It is certified that error appears in the above-identified patent and that said Letters Patent is hereby corrected as shown below:

The Claims should be amended to:

(1) Column 33, line 33, Claim 4, replace ulcerative colitis with Crohn's disease

(2) Column 33, line 34, Claim 5, replace wherein the ulcerative colitis is moderately to severely active and exhibits a Mayo score not less than about 6 with wherein the Crohn's disease is active and exhibits an activity index not less than about 220

(3) Column 33, line 37, Claim 6, replace The method of claim 3, wherein the inflammatory bowel disease is Crohn's disease with The method of claim 5, wherein the compound is administered according to a regimen effective to achieve clinical remission of the Crohn's disease

(4) Column 33, line 39, Claim 7, replace The method of claim 6, wherein the Crohn's disease is active and exhibits an activity index not less than about 220 with The method of claim 4, wherein the Crohn's disease is fistulizing Crohn's disease

(5) Column 34, line 1, Claim 8, replace The method of claim 7, wherein the compound is administered according to a regimen effective to achieve clinical remission of the Crohn's disease with The method of claim 4, wherein the subject is a pediatric patient

(6) Column 34, line 4, Claim 9, replace The method of claim 6, wherein the Crohn's disease is fistulizing Crohn's disease with The method of claim 3, wherein the inflammatory bowel disease is ulcerative colitis

(7) Column 34, line 6, Claim 10, replace The method of claim 6, wherein the subject is a pediatric patient with The method of claim 9, wherein the ulcerative colitis is moderately to severely active and exhibits a Mayo score not less than about 6

Signed and Sealed this
Fifth Day of July, 2011

David J. Kappos
*Director of the United States Patent and Trademark Office*